(12) United States Patent
Haneef et al.

(10) Patent No.: US 9,080,907 B2
(45) Date of Patent: Jul. 14, 2015

(54) SHEAR STRESS SENSORS

(75) Inventors: Ibraheem Haneef, Lahore (PK);
Howard P. Hodson, Godmanchester (GB); Robert Miller, Cambridge (GB); Florin Udrea, Cambridge (GB)

(73) Assignee: Cambridge Enterprise Limited, Cambridge, Cambridgeshire (GB)

( * ) Notice: Subject to any disclaimer, the term of this patent is extended or adjusted under 35 U.S.C. 154(b) by 1328 days.

(21) Appl. No.: 12/739,520

(22) PCT Filed: Oct. 24, 2008

(86) PCT No.: PCT/GB2008/050995
§ 371 (c)(1),
(2), (4) Date: Jun. 1, 2010

(87) PCT Pub. No.: WO2009/053757
PCT Pub. Date: Apr. 30, 2009

(65) Prior Publication Data
US 2010/0242592 A1      Sep. 30, 2010

(30) Foreign Application Priority Data

Oct. 25, 2007      (GB) .................................. 0720905.9

(51) Int. Cl.
*G01F 1/68* (2006.01)
*G01F 1/684* (2006.01)
(Continued)

(52) U.S. Cl.
CPC ............ *G01F 1/6845* (2013.01); *G01F 1/7084* (2013.01); *G01N 3/24* (2013.01); *G01N 2203/0226* (2013.01); *G01N 2203/0623* (2013.01)

(58) Field of Classification Search
USPC ....................................................... 73/204.26
See application file for complete search history.

(56) References Cited

U.S. PATENT DOCUMENTS 5,883,310 A * 3/1999 Ho et al. ......................... 73/766
6,326,229 B1 * 12/2001 Mastromatteo et al. ........ 438/49
(Continued)

FOREIGN PATENT DOCUMENTS

DE          4228484 A1     3/1994
EP          0 882 978 A1   12/1998
(Continued)

OTHER PUBLICATIONS

Liu, et al., "A Micromachined Flow Shear-Stress Sensor Based on Thermal Transfer Principles", "Journal of Microelectromechanical Systems", Mar. 1999, pp. 90-99, vol. 8, No. 1, Publisher: IEEE, Published in: U.S.

(Continued)

*Primary Examiner* — Lisa Caputo
*Assistant Examiner* — Jamel Williams
(74) *Attorney, Agent, or Firm* — Loginov & Associates, PLLC; William A. Loginov

(57) ABSTRACT

This invention relates to hot film shear stress sensors and their fabrication. We describe a hot film shear stress sensor comprising a silicon substrate supporting a membrane having a cavity underneath, said membrane bearing a film of metal and having electrical contacts for heating said film, and wherein said membrane comprises a silicon oxide membrane, where in said metal comprises aluminium or tungsten, and wherein said membrane has a protective layer of a silicon-based material over said film of metal. In preferred embodiments the sensor is fabricated by a CMOS process and the metal comprises aluminium or tungsten.

21 Claims, 17 Drawing Sheets

(51) Int. Cl.
*G01F 1/708* (2006.01)
*G01N 3/24* (2006.01)

(56) References Cited

U.S. PATENT DOCUMENTS

| | | | |
|---|---|---|---|
| 6,361,206 B1 * | 3/2002 | Bonne | 374/138 |
| 6,523,403 B1 * | 2/2003 | Fuertsch et al. | 73/204.26 |
| 7,367,237 B2 * | 5/2008 | Hsiai et al. | 73/841 |
| 2006/0154401 A1 | 7/2006 | Gardner et al. | |
| 2007/0231942 A1 * | 10/2007 | Vanha et al. | 438/50 |

FOREIGN PATENT DOCUMENTS

| | | | | |
|---|---|---|---|---|
| EP | 1092962 A2 * | 4/2001 | | G01F 1/684 |
| EP | 1327869 A1 | 7/2003 | | |
| WO | WO 2007034240 A2 | 3/2007 | | |
| WO | 2009048918 A1 | 4/2009 | | |
| WO | WO 2009053757 A2 * | 4/2009 | | G01F 1/684 |

OTHER PUBLICATIONS

Laconte, et al., "Fully CMOS-SOI Compatible Low-Power Directional Flow Sensor", "Proceedings of IEEE Sensors, 2004", Oct. 24, 2004, pp. 864-967, Publisher: IEEE, Published in: US.

Laconte, et al., "SOI CMOS Compatible Low-Power Microheater Optimization and Fabrication for Smart Gas Sensor Implementations", "Proceedings of IEEE Sensors 2002", Jun. 12, 2002, pp. 1395-1400, Publisher: IEEE, Published in: US.

\* cited by examiner

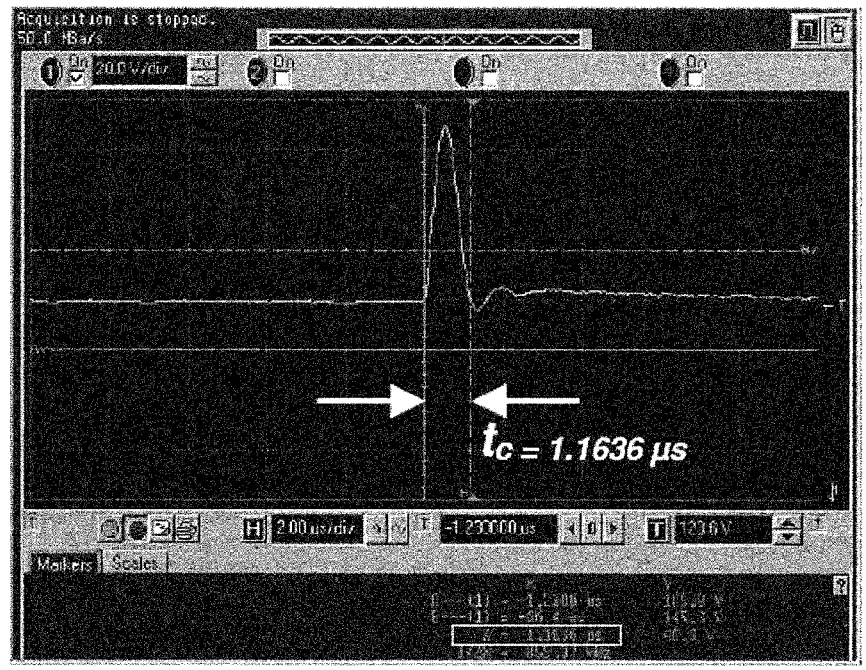
Figure 7c
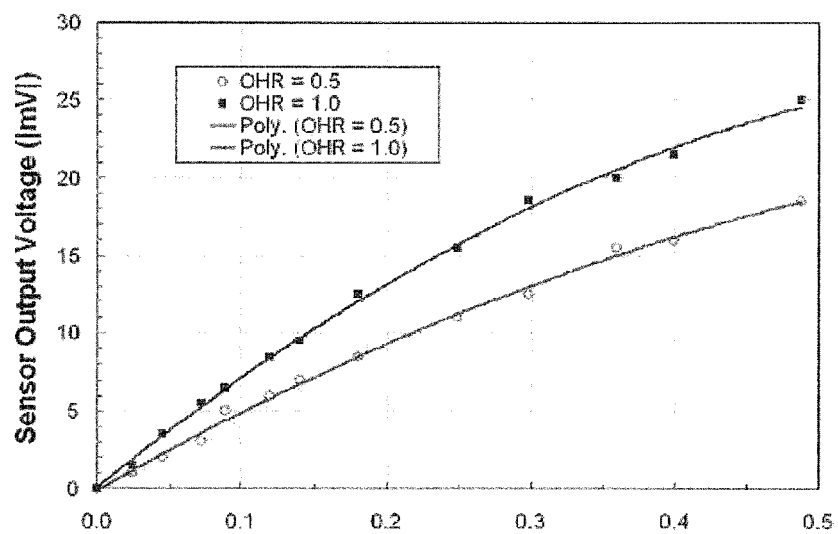
Figure 7d  Wall Shear Stress (Pa)

SHEAR STRESS SENSORS

FIELD OF THE INVENTION

This invention relates to hot film shear stress sensors and their fabrication.

BACKGROUND TO THE INVENTION

A fluid flowing past a solid boundary exerts a shear stress on it due to the viscosity of the fluid. Measurement of this shear stress 'τ' is of much interest to fluid dynamics research community since knowledge of variation in wall shear stress is often very useful in analyzing a flow field.

The wall shear stress measurement techniques can be segregated into direct and indirect methods (T. J. Hanratty and J. A. Campbell, "Measurement of Wall Shear Stress" in Fluid Mechanics Measurements, 2nd ed., R. J. Goldstein E., Taylor & Francis, USA 1996, pp. 575-648).

Detailed reviews of wall shear stress measurement techniques based on conventional macro scale sensors (T. J. Hanratty and J. A. Campbell, "Measurement of Wall Shear Stress" in Fluid Mechanics Measurements, 2nd ed., R. J. Goldstein E., Taylor & Francis, USA 1996, pp. 575-648; J. H. Haritonidis, "The Measurement of Wall Shear Stress," in Advances in Fluid Mechanics Measurements, M. Gad-El-Hak Ed., Springer-Verlag, 1989 pp. 229-261; K. G. Winter, "An outline of the techniques available for the measurement of skin friction in turbulent boundary layers," Prog., Aeronaut. Sci., vol. 18, pp. 1-57, 1977) and MEMS based sensors (L. Löfdahl, and M. Gad-el-Hak, "MEMS based pressure and shear stress sensors for turbulent flows," Meas. Sci. Technol., vol. 10, pp. 665-686, 1999; L. Löfdahl, and M. Gad-el-Hak, "MEMS applications in turbulence and flow control," Prog. Aerospace Sci., vol. 35, pp. 101-103, 1999; J. Naughton, and M. Sheplak, "Modern developments in shear-stress measurement," Prog. Aero. Sci., vol. 38, pp 515-570, 2002; M. Sheplak, L. Cattafesta, and T. Nishida, "MEMS Shear Stress Sensors: Promise and Progress," AIAA paper 2004-2006, Proc. 24th AIAA Aerodynamic Measurement Technology and Ground Testing Conference, Portland, Oreg., 28 Jun. 1 Jul., 2004) have been published.

Among the indirect methods the development of thermal shear stress sensors has seen significant advancement in recent years (E. Kälvesten. "Pressure and wall shear-stress sensors for turbulence measurements," PhD thesis, KTH, Sweden, 1996; C. Liu, C-B. Huang, Z. Zhu, F. Jiang, S. Tung, Y-C. Tai and C-M. Ho, "A micromachined flow shear-stress sensor based on thermal transfer principles," J. Microelectricalmech. Syst., vol. 8, pp. 90-99, 1999; M. Sheplak, V. Chandrasekaran, A. Cain, T. Nishida, and L. Cattafesta, "Characterisation of a micromachined thermal shear-stress sensor," AIAA J., vol. 40, pp. 1099-1104, 2002; S. Tung, H. Rokadia, and W. J. Li, "A micro shear stress sensor based on laterally aligned carbon nanotubes," Sensors and Actuators A:Physical, vol. 133, pp. 431-438, 2007; M. Kimura, S. Tung, J. Lew, C-M Ho, F. Jiang and Y-C Tai, "Measurements of wall shear-stress of a turbulent boundary layer using a micro-shear stress imaging chip," Fluid. Dyn. Res., vol. 24, pp. 329-342, 1999; J-B Huang, Z. Zhu, F. Jiang, Y-C Tai, and C-M Ho, "A micro-electro-mechanical-system-based thermal shear-stress sensor with self-frequency compensation," Meas. Sci. Technol., vol. 10, pp. 687-696, 1999; Y. Xu, Y-C. Tai, A. Huang and COM. Ho, "IC-integrated flexible shear-stress sensor skin," J. Microelectromech. Syst., vol. 12, pp. 740-747, 2003). The integration of CTA—Constant temperature anemometry (CTA) and constant current anemometry (CCA) circuits with polysilicon based shear stress sensors is described in X-Q. Qang/Wang, Z. Han, F. Jiang, T. Tsao, Q. Lin, Y-C. Tai, V. Koosh, R. Goodman, J. Lew, and C-M Ho, "A fully integrated shear-stress sensor," Proceedings of Transducers 99, pp. 1074-1077, 1999.

The sensors described above have been developed using various materials as sensing elements (e.g. polysilicon (E. Kälvesten. "Pressure and wall shear-stress sensors for turbulence measurements," PhD thesis, KTH, Sweden, 1996; C. Liu, C-B. Huang, Z. Zhu, F. Jiang, S. Tung, Y-C. Tai and C-M. Ho, "A micromachined flow shear-stress sensor based on thermal transfer principles," J. Microelectricalmech. Syst., vol. 8, pp. 90-99, 1999; M. Kimura, S. Tung, J. Lew, C-M Ho, F. Jiang and Y-C Tai, "Measurements of wall shear-stress of a turbulent boundary layer using a micro-shear stress imaging chip," Fluid. Dyn. Res., vol. 24, pp. 329-34-2, 1999; Y. Xu et al ibid, platinum (M. Sheplak, V. Chandrasekaran, A. Cain, T. Nishida, and L. Cattafesta, "Characterisation of a micromachined thermal-shear stress sensor," AIAA J., vol. 40, pp. 1099-1104, 2002), laterally aligned carbon nanotubes (CNTs) (S. Tung, H. Rokadia, and W. J. Li, "A micro shear stress sensor based on laterally aligned carbon nanotubes," Sensors and Actuators A: Physical, vol. 133, pp. 431-438, 2007)). Diverse thermal isolation schemes have also been employed (e.g. polyimide filled KOH-etched trench (E. Kälvesten. "Pressure and wall shear-stress sensors for turbulence measurements," PhD thesis, KTH, Sweden, 1996), surface micro-machined vacuum cavity under silicon nitride diaphram (C. Liu, C-B. Huang, Z. Zhu, F. Jiang, S. Tung, Y-C. Tai and C-M. Ho, "A micromachined flow shear-stress sensor based on thermal transfer principles," J. Microelectromech. Syst., vol. 8, pp. 90-99, 1999), and wafer-bonded vacuum cavity under silicon nitride diaphram (M. Sheplak, V. Chandrasekaran, A. Cain, T. Nishida, and L. Cattafesta, "Characterisation of a micromachined thermal shear-stress sensor," AIAA J., vol. 40, pp. 1099-1104, 2002). However thermal isolation could be improved.

Further background prior art can be found in: US2006/0081064; US2005/0021247; US2003/0199116; U.S. Pat. Nos. 6,071,819; 5,511,428; and 5,291,781.

In this specification we are particularly concerned with hot film shear stress sensors. In this type of sensor a film of material is located at the edge of the fluid flow, typically inset into a wall or other boundary. The film is heated to above the ambient temperature of the fluid, for example by a few tens of degrees centigrade, by passing electrical current through it. The rate of heat loss from a heated hot-film to the air flow is dependent on the velocity profile in the boundary layer and the viscosity of the fluid. The shear stress 'τ' is mathematically defined as:

$$\tau = \mu(dU_y/dy) \quad (1)$$

where 'μ' is the fluid viscosity and '$U_y$' is the flow velocity at a distance 'y' from the wall. As a result, the flow shear stress determines the rate of heat transfer from the heated element to the surrounding flow field. The temperature change of the hot film can be measured by monitoring the change in its resistance. The resistance of a hot film is given by the relationship:

$$R = R_0(1 + \alpha(T - T_0)) \quad (2)$$

where 'R' and '$R_0$' are sensor electrical resistance values at a higher and ambient (or a reference) temperature respectively, 'α' is hot film's temperature coefficient of resistance (TCR) and 'T' and '$T_0$' are the film's temperature and the ambient (or reference temperature), respectively.

To measure the shear stress, the following relationship (T. J. Hanratty and J. A. Campbell, "Measurement of Wall Shear Stress," in Fluid Mechanics Measurements, 2nd ed., R. J. Goldstein Ed., Taylor & Francis, USA, 1996, pp. 610-612) is used:

$$(I^2R)/(T-T_0)=A(\rho\tau^{1/n})+B \quad (3)$$

where 'I' is the electrical current through the hot film, 'R' is the hot film's electrical resistance, $\Delta T$ is the hot film temperature rise from ambient or a reference temperature, 'ρ' is fluid density and 'A', 'B' and 'n' are constants that are determined experimentally through a calibration procedure. Effectively the term A ($\rho\tau^{1/n}$) signifies the heat loss into fluid through convection and B signifies the heat loss to the substrate through conduction.

Three type of driving anemometry circuits are commonly used for sensor operation. These are known as constant temperature (CT), constant current (CC) and constant voltage (CV) circuits and details of these are well-known to those skilled in the art.

Background prior art can be found in U.S. Pat. Nos. 5,883,310, 6,071,819, 6,953,982, 6,825,539, 6,511,859, 5,243,858, and US 2006/0154401.

It would be desirable to be able to employ a CMOS manufacturing process to fabricate a hot film shear stress sensor. In particular this offers the promise of reduced manufacturing costs, option of circuit integration on the same chip, reproducible sensor geometry and characteristics, mass production, and reliable sensor performance There have been few attempts to design CMOS hot film shear stress sensors in past (ibid, X-Q. Wang et al ibid; and Y. Xu ibid). However, these have employed polysilicon as a sensing material. Compared to metals (e.g. tungsten, aluminium), polysilicon has some significant disadvantages when used as a hot film shear stress sensor: it has a lower TCR, a lower thermal operating range as its resistance starts to change/drift at higher temperatures, higher impedance, significant 1/f noise (S.-L. Jang, "A model of 1/f noise in polysilicon resistors," Solid-State Electronics, 33, 1155-1162, 1990) and much higher coefficient of piezo-resistivity which causes piezo-resistivity induced resistance changes in the sensor in addition to shear stress induced resistance variations.

SUMMARY OF THE INVENTION

According to the present invention there is therefore provided a hot film shear stress sensor comprising a silicon substrate supporting a membrane having a cavity underneath, said membrane bearing a film of metal and having electrical contacts for heating said film, and wherein said membrane comprises a silicon oxide membrane, wherein said metal comprises aluminium or tungsten, and wherein said membrane has a protective layer of a silicon-based material over said film of metal.

In preferred embodiments the sensor is fabricated by a CMOS process and the cavity is formed by DRIE (deep reactive ion etching). This facilitates inexpensive manufacture of the sensor. In preferred embodiments the metal of the hot film comprises part of the same metal layer (or layers) which is (or are) employed for the electrical contacts employed for heating the film and for sensing. Thus these may be fabricated in the same CMOS fabrication sequence.

In some preferred embodiments the metal comprises aluminium. Hitherto there has been a particular prejudice in the art against the use of aluminium because of its perceived significant problems including rapid degeneration at elevated temperatures due to oxidation, and electromigration. However surprisingly the inventors have found that aluminium is effective and stable in a shear stress sensor and has some useful advantages as a sensing material (described in more detail later). In embodiments a layer of silicon oxide or nitride protects the metal, more particularly aluminium or tungsten of the hot film. Thus in embodiments, the hot metal film is sandwiched between two oxide layers and is effectively embedded in $SiO_2$.

In embodiments two or more stacked metal layers, optionally in electrical contact, may be employed to provide the metal film. For example, crossed sensors may be employed to detect perpendicular components of shear stress; these crossed sensors may comprise two sensors, one in each metal layer. Preferably a lateral dimension of a sensor is appropriate to the scale at which differences in shear stress, for example due to vortices, eddies and other flow structures, are to be investigated. For a gas the length scale may be 1-200 μm; for blood, for example, 50-100 μm. When sensing blood it is preferable to use relatively thicker films, to reduce resistive heating and hence keep the temperature of the sensor in operation below that at which damage to the blood would otherwise occur.

In embodiments sensing elements in the different metal layers may have different shapes, for example extending in substantially a single dimension in one layer and in two dimensions in a second layer. The sensing elements in the different metal layers may be substantially electrically isolated from one another. In embodiments a metal layer may be patterned to provide a heat spreading plate around part or all of the sensor, for example to define a plate in the shape of a loop around the sensing element. This may be connected electrically to the sensing element to provide redundancy in the event of electrical failure of the sensing element.

In embodiments the film of metal may be provided with a heat sink, for example in the form of a plurality of vertically extending structures such as fins, vertical pins and the like. In embodiments the heat sink may comprise vertically arranged or entangled carbon nanotubes (CNTs). There may be grown in-situ on the metal film by published techniques. The metal film on which the CNTs are grown may advantageously be heated during CNT growth. A method according to the invention may comprise forming a heat sink on the sensor, in particular at least partially virtually aligned growing CNTs on the sensor. Alternatively a heat sink may comprise a surface profile or texture applied to the metal film.

Optionally one or more oxide layers may also be employed for either or both of the membrane and protective layer. The skilled person will understand that, according to the application, a range of different thicknesses and shapes of the metal film may be employed including rectangular, circular, elliptical, and longitudinal shapes. Where two or more metal layers are employed the upper layer may have a different shape and/or a different, for example larger or smaller, surface area to the lower layer, this also providing increased sensitivity.

A meander, circular or rectangular pattern may be defined in the film, for example by etching during a standard CMOS fabrication sequence. Additionally or alternatively the metal film may be configured for four-terminal resistance sensing, in which case four electrical contacts may be provided for the film. By using four probe resistance sensing, exact resistance of the hot film can be monitored during sensor operation and by monitoring these resistance changes, temperature of the sensor can be determined with help of Eqn (2). In still other embodiments a dedicated temperature sensor such as a CMOS thermistor or diode may be fabricated in close proximity to the hot film (for example, in an adjacent layer).

In some preferred embodiments, the sensor comprises a silicon-on-insulator (SOI) CMOS sensor. In embodiments, interface electronics for the sensor may be fabricated on a single, common substrate with the sensor. This interface electronics may comprise, for example, a control loop and configured to drive the sensor to maintain the film at a constant temperature (CT) above an ambient temperature of the sensed fluid. The alternate driving circuits can also be fabricated on the sensor chip to drive the sensor at constant voltage (CV) or constant current (CC).

The invention also provides a method of shear stress sensing using a hot film, the method employing a hot film shear stress sensor as described above. The method may be employed for shear stress sensing in air, or a liquid such as blood or another body fluid and more generally in other biological applications. Again the skilled person will appreciate that routine experiment may be employed to determine optimum parameters (size and shape of the hot metal film; the thickness is generally set by the CMOS process employed) for a particular application.

In a related aspect the invention provides a method of fabricating a hot film shear stress sensor on a silicon substrate, the method comprising: fabricating a layer of silicon oxide in a sensing region of said substrate; fabricating a film of metal on said layer of silicon oxide on said sensing region, said metal comprising aluminium or tungsten; fabricating electrical contacts for said film; using deep reactive ion etching to undercut said layer of silicon oxide to leave a cavity underneath; and fabricating a protective layer over said film of metal.

A shear stress sensor as described above, in particular in the embodiments described later, is also usable as a time-of-flight (TOF) sensor, for example in microfluidics applications. Thus the invention also provides a TOF sensor having features as described above and/or as described later; and a method of fabricating such a sensor.

A shear stress sensor as described above, in particular in the embodiments described later, is also usable as a mass or volume shear rate sensor, eg for automotive applications, for example air flow into the engine air input manifold, or for heating/ventilation or air conditioning systems, for example to maintain a constant flow rate. Tungsten sensors—as described later—may advantageously be employed in such applications. For example a small (~20 m square) tungsten sensor had an approximately linear response with the rates up to at least 70 liters/minute, which gave 135 mV output.

The invention also provides a macroscale shear stress sensor array, preferably using sensors of type described herein, over an area of >0.1 m×>0.1 m.

In a further aspect the invention provides a MEMS aspirating sensor comprising a silicon substrate supporting a membrane having a cavity underneath, said membrane having an aperture for fluid flow vertically through the sensor, the sensor including a metal conductor disposed across said aperture.

BRIEF DESCRIPTION OF THE DRAWINGS

These and other aspects of the invention will now be further described by way of example only, with reference to the accompanying figures in which:

FIGS. 7a to 7d show, respectively, the temperature coefficient of resistance (TCR) of the tungsten wall shear stress sensor. The experimentally determined value of TCR for the sensor is 0.206%/° C.; comparison of the calculated sensor temperature at various power inputs for a sensor on SOI membrane with the one on SOI substrate—the sensor achieves 100° C. temperature at a nominal power input of 2.0 mW (2.6 mW with the power tracks); square wave response of the tungsten hot-film sensor at a resistive over-heat ratio of 0.5. The measured time constant ($t_c$) is 1.1636 μs, which corresponds to a cut-off frequency ($f_c$=1/1.3 $t_c$) of 661 kHz; and sSensor output voltages vs wall shear stress at resistive over-heat ratios of 0.5 and 1.0 in CTA mode—the sensor exhibits a time constant of 1.2 μs at overheat ratio of 0.5 with a corresponding cut-off frequency of 661 kHz, the best ever reported time constants for thermally isolated micro hot-film shear stress sensor; at a resistive overheat ratio of 1.0, the sensor calibration in a 2-D flow channel has demonstrated an average sensitivity of 65 mV/Pa in CTA mode for a wall shear stress range of 0-0.49 Pa;

DETAILED DESCRIPTION OF ILLUSTRATIVE EMBODIMENTS

Figure 1A:
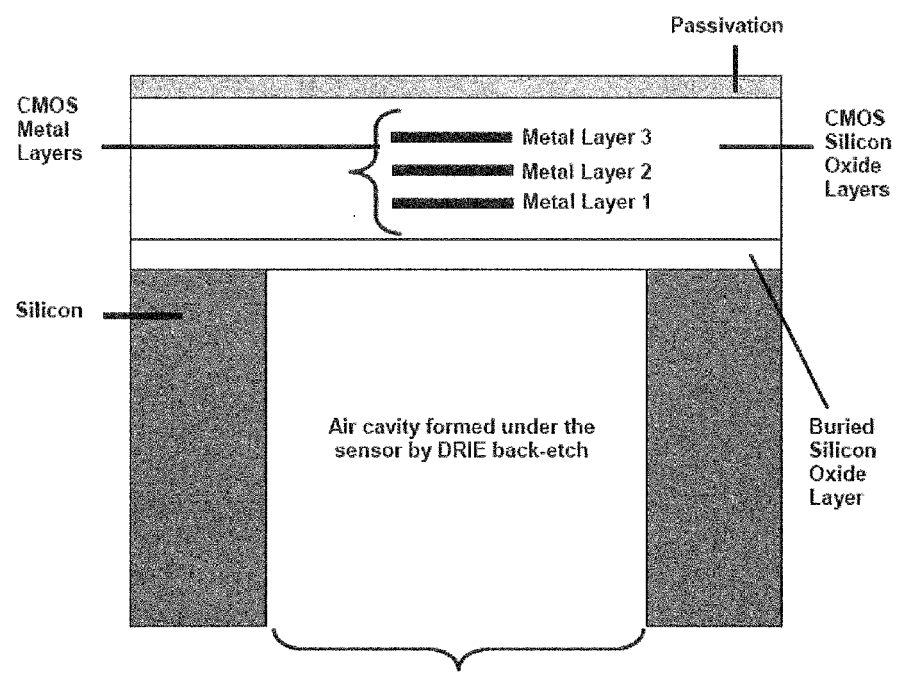
FIGS. 1a to 1d show, respectively, a vertical cross-section through an embodiment of a CMOS wall hot film shear stress sensor according to the invention, showing more than one metal layer embedded in silicon oxide layers, in which a meander shape sensor has been fabricated from metal layer 1 and metal layers 2 and 3 have been used for sensor power supply and 4-probe resistance measurement tracks as well as contact pads; and an optical micrograph showing a view from above of a fabricated aluminium shear stress sensor on a silicon oxide membrane; a packaged sensor; and an optical micrograph of a CMOS tungsten shear stress sensor on a DRIE SOI membrane (tungsten resistor element size 120 μm×2 μm×0.55 μm; oxide membrane diameter—of the circle in the Figure—360 μm)
Figure 1B:
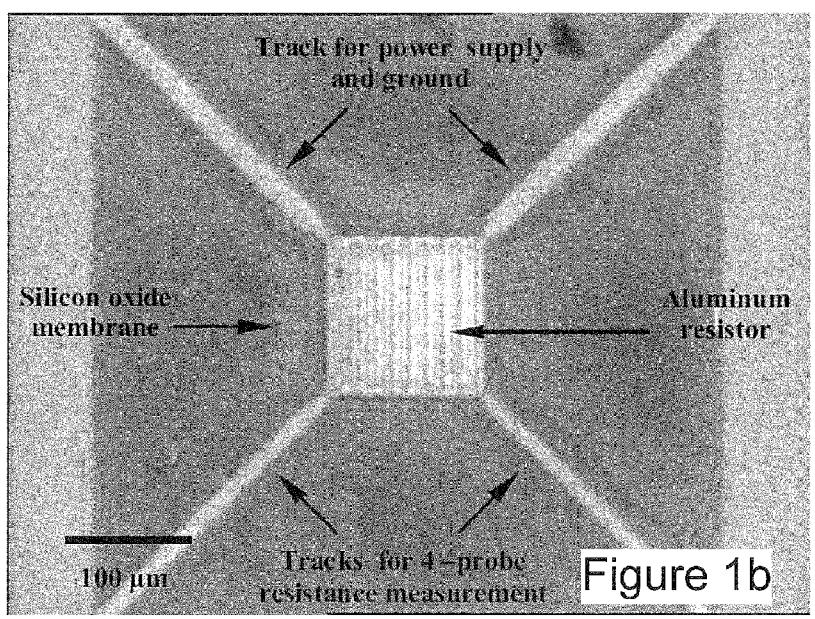

Broadly speaking, we will describe a novel silicon on insulator (SOI) complementary metal oxide semiconductor (CMOS) thermal shear stress sensor for turbulent flow measurements based on an aluminium or tungsten hot film as a sensing element. Both aluminium and tungsten are used for the metallization and interconnects in the CMOS electronics and does not suffer any piezo-resistivity induced pressure sensitivity. Moreover, both these metals are very stable at higher temperatures (e.g. aluminium based sensor is stable up to 250° C. whereas tungsten based sensors can give very stable performance up to 800° C.). These devices have been fabricated using a 1 µm SOI-CMOS process followed by a deep reactive ion etch (DRIE) back-etch stop, offering low cost and the option of circuit integration. The DRIE process has been used for forming of oxide membranes under micro hot film shear stress sensors and for successful thermal isolation of the sensors. For illustration of sensor performance, we shall use only one particular design of sensor, whose vertical cross section and a top view micrograph is shown in FIGS. 1(a) and 1(b) respectively. This is an aluminium based sensor embedded in silicon oxide layers in a meander shape. It is important to mention that the sensors' shape and geometrical dimensions, as well as size and shape of silicon oxide membranes formed by removing silicon through DRIE underneath the sensor may be changed to optimise sensor performance for different applications and different characteristics.

The meander shaped aluminium sensors described here as an example, have a good spatial resolution (size 130 µm×130 µm) and a very efficient thermal isolation (due to their location on a 500 µm×500 µm, low thermal conductivity silicon oxide membrane). Results show that these sensors have a high temperature coefficient of resistance (TCR) (0.319%/° C.), a low power consumption (below 10 mW for 100° C. temperature rise) and a high reproducibility within a wafer and from wafer to wafer. In constant temperature (CT) mode, the sensors exhibit an average sensitivity of 22 mV/Pa in a wall shear stress range of 0-1.5 Pa and an ultra-short time constant of only 13.8 µs, which corresponds to a high cut-off frequency of 48 KHz.

Sensor Design

The sensor was designed using a Cadence™ Virtuoso® custom design platform. A meander shape aluminium sensor was designed which covers an area of 130 µm×130 µm so as to have a small resolution for turbulent flow measurements. For effective thermal isolation, the sensor was located in the centre of the silicon oxide membrane. The membrane has a size 500 µm×500 µm and was formed by a post CMOS, DRIB back-etch. In other embodiments, tungsten may be employed in place of aluminium. Both metals are compatible with the CMOS process and so in either case, the same metal may be employed for the hot film as is used for the metallization.

FIG. 1a shows a vertical cross-section through a hot film shear stress sensor according to an embodiment of the invention, illustrating details of the structure. The substrate is an SOI wafer with a silicon layer on top of buried silicon dioxide ($SiO_2$) layer and silicon handle layer. During the CMOS fabrication process, alternative layers of metal (i.e. aluminium or tungsten) and silicon dioxide are deposited. For this particular sensor, only one metal layer has been used for making a meander shaped resistive track for shear stress sensing. In the illustrated example there are up to three metal layers available for defining a sensing hot film, each sandwiched between silicon oxide layers. The other metal layers have been used to form metal interconnects for sensor power supply and 4-probe resistance measurement. Depending upon performance and application requirements, we may choose to use either or all of these metal layers. As shown in the figure, a passivation layer (e.g. silicon nitride) is also deposited on top of the upper silicon oxide layer so that sensor is fully embedded between the silicon oxide layers. The air cavity under the sensor has been created by using a post-CMOS, DRIE back-etch process.

The top view (micro graph) of an actual meander shaped hot film sensor has been shown in FIG. 1b. Typical cold resistance of these meander shaped aluminium hot film shear stress sensors (e.g. the one shown in FIG. 1b) is 20Ω, which gives them the advantage of being useable with commercially available constant temperature anemometer circuits. The sensor track is 3 μm wide and 720 nm thick. Total track length of the sensor is 1300 μm. The sensor track's width and length may be varied according to the different applications. The alternate widths and total track lengths could have any value between 1 μm to 20 μm and 40-2000 μm, respectively to achieve different resistance values so that these sensors could be operated readily with different commercially available or purpose built CT, CV or CC anemometry circuits. The sensor width and length may be varied to make it most suitable for different applications (i.e. the best width and length of the sensor could vary for measuring shear stress of different fluids e.g. air, water, blood etc. and for measurements at different flow speeds or Reynolds Number).

Sensor Fabrication

The micro hot film shear stress sensors were fabricated in a SOI-CMOS process employing aluminium and tungsten metallization. After fabrication, the silicon oxide membranes were formed by a DRIE back-etch at a MEMS foundry. Metal alignment marks for the silicon oxide membranes were used for accurate back to front alignment and to minimise the under-cut effect of the DRIE.

Thermal and Electrical Characterization.

The temperature coefficient of resistance for the aluminium hot film sensors was determined by heating a finished wafer on a Signatone® model S-1060R QuieTemp DC hot chuck system and measuring the change in sensor resistance with help of a Keithley® model 2400 source meter. The measurements were made for 20-300° C. and repeated for different wafers to see the data reproducibility. The sensor I-V characterisation was done using a Hewlett Packard 4142B modular DC source/monitor and a Signatone® model S-1160 probe station.

Sensor Packaging and Wind Tunnel Set Up

Figure 1C:
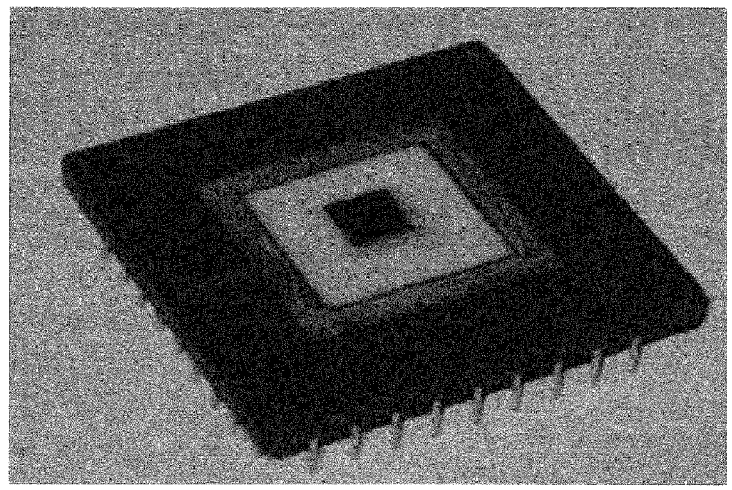
Figure 1D:
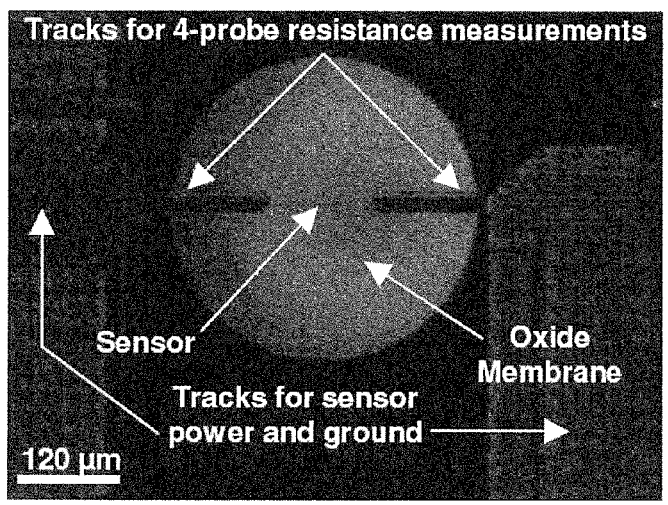

The sensor chip was gold wire bonded onto a commercial ceramic pin grid array package using a Kulicke & Soffa® model 4123 wedge bonder. The cavity around the sensor was filled with GE Silicones® RTV 11 silicon rubber compound to achieve an aerodynamically smooth surface (FIG. 1c).

The packaged sensor was surface flush mounted in an experimental wind tunnel, which is 50 cm wide, 2.5 cm high and 2.5 m long. Pressure taps at a distance of 18 cm each were kept in the mid-span of wind tunnel top wall, all along the wind tunnel length, to record the pressure drop in the flow direction. The wall shear stress was calculated by measuring the pressure drop along the wind tunnel length.

Sensor Arrays

The sensors were used in a macroscale array, over an area of >0.1 m×>0.1 m, for example 0.5 m×0.75 m. A (macroscale) sensor array was fabricated as follows: The MEMS sensor chips were wire bonded onto a cavity within PCB strips using a Kulicke & Soffa® model 4123 wedge bonder. The cavities around the sensors were filled with an adhesive to achieve an aerodynamically smooth surface. These PCBs with MEMS sensors were then flush-mounted onto a thin aluminium sheet for final mounting in a low speed wind tunnel. In one example an array of 16 large and 11 small CMOS shear stress sensors was flush mounted in a low speed wind tunnel for flow transition measurement experiment.

Sensor Calibration and Performance Characterisation.

The sensor was biased with help of a Dantec Dynamics® model 56C17 constant temperature anemometer (CTA) wheatstone bridge and 56C01 CTA unit. The sensor output voltage was measured at different resistive overheat ratios and shear stress levels (from 0-15 Pa). To estimate the frequency response of the sensor, a square wave was injected at the top of the bridge and the corresponding response was captured on an Agilant Technologies® Infniium model 54810 oscilloscope.

Temperature Coefficient of Resistance

Figure 2:
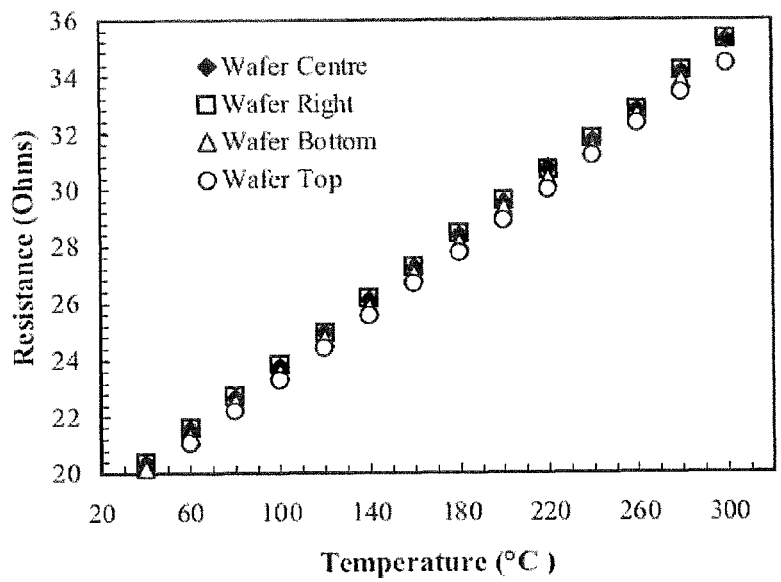
FIG. 2 shows the temperature coefficient of resistance (TCR) of aluminium shear stress sensing resistors at four different locations on a wafer.

The temperature coefficient of resistance determined for four sensors at different locations on the same wafer is shown in FIG. 2. The sensors exhibit a TCR of 0.319%/° C. which is the best value reported in literature for micro/nano thermal shear stress sensors (e.g. TCR reported for polysilicon, platinum and laterally aligned CNTs based shear stress sensors was 0.13%/° C., 0.29%/° C. and 0.04%/° C., respectively. Moreover aluminium and tungsten have a negligible piezoelectric effect.

I-V Characteristics

Figure 3:
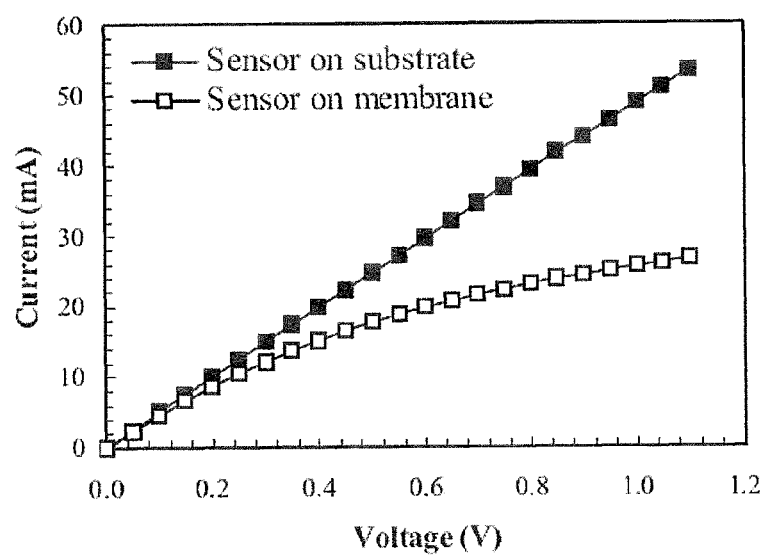
FIG. 3 shows a comparison of I-V characteristics of a sensor on a substrate with a sensor on a silicon oxide membrane, the linear I-V curve for the sensor on the substrate indicating a stable resistance due to most of the power being lost via thermal conduction to the substrate.

The I-V characteristics of the sensor on the SOI oxide membrane compared with a sensor on a bulk SOI substrate (FIG. 3) show significant non-linearity for the former, indicating a strong joule heating effect.

Thermal Isolation

Figure 4:
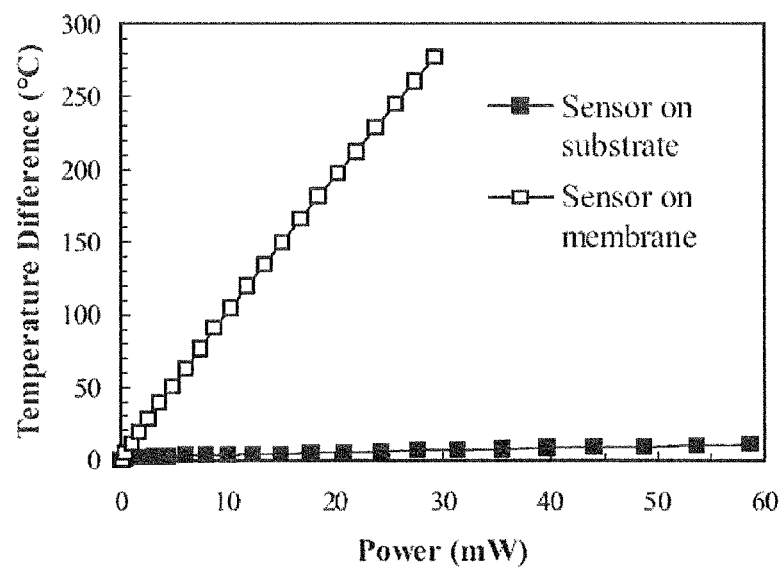
FIG. 4 shows a graph of temperature rise against power input comparing a sensor on a silicon oxide membrane with a sensor on an SOI substrate illustrating that, for example, for an input power of 20 mW the temperature rise of the sensor on the membrane is 200° C. compared with 5° C. for a sensor on the substrate.

The effectiveness of the oxide membrane as a thermal isolator of the sensor is shown in FIG. 4 which compares the temperature rise in a sensor located on bulk SOI substrate with the one thermally isolated by means of a back DRIB step and creation of a silicon oxide membrane underneath. The results confirm that the thermal resistance of sensor on membrane (i.e. 9488° C./Watt) is more than 50 times better than that for a sensor on substrate (i.e. 187° C./Watt). We find an oxide membrane to be more effective for thermal isolation of a hot film sensor than a silicon nitride (SiN) membrane of same thickness and dimensions as the typical value of thermal conductivity for silicon oxide is only 1.4 W/m K compared to 19 W/m K for SiN.

Wall Shear Stress Sensitivity

Figure 5:
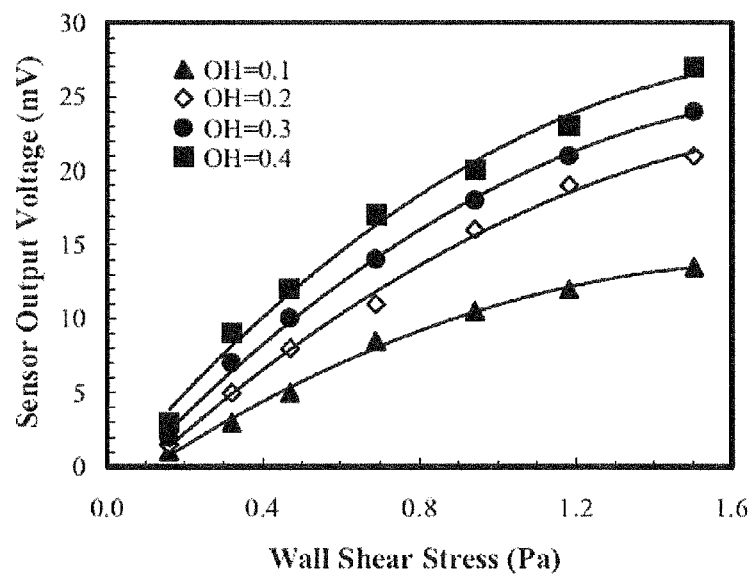
FIG. 5 shows graphs of sensor output voltage against wall shear stress for different resistance overheat (OH) ratios in a constant temperature (CT) mode showing that sensitivity increases at higher overheat ratios.

The sensor was calibrated in the wind tunnel at different resistive overheat ratios in CT mode using the CTA unit. The resistive overheat ratio $\alpha_R$ is defined as:

$$\alpha_R = (R-R_0)/R_0 \quad (1)$$

where R is the sensor resistance at the higher temperature due to Joule heating and $R_0$ is the sensor resistance at room temperature prior to any Joule heating. The steady state sensor output voltage at different flow velocities (and corresponding different mean shear stress values) was measured. The calibration results are shown in FIG. 5. The sensor sensitivity to shear stress increases with the increase in resistive over heat ratio. At an overheat ratio of 0.4, the sensor exhibits and average sensitivity of 22 mV/Pa for a wall shear stress range of 0-1.5 Pa.

Laminar/Turbulent Flow Detection

Embodiments of the sensors work by heat conducted away from the sensor. During a transition of flow from laminar to turbulent the output (voltage) from the sensor rises. This is because of a rise in the velocity of the flow near the sensor and the associated increase of the skin friction drag. If laminar flow separation occurs the output (voltage) from the sensor is lowest where the flow adjacent to sensor is at substantially zero velocity. If there is subsequent transition to turbulent flow and the flow reattaches to the surface, the sensor output then increases, sometimes becoming larger that achieved with laminar flow, because turbulent flow is often better at conducting heat away. The mean or RMS (root mean square) sensor output voltage may be employed to effectively measure the quasi-wall shear stress; the sensor may be large (>100 µm square) or small (<20 µsquare). It will be appreciated that the boundary between laminar and turbulent flow may be identified by identifying the point of substantially minimum output from a sensor. This is particularly useful for sensing at a macro-scale, that is over length (or area) scales of >0.1 m, >0.5 m or >1 m.

Frequency Response

Figure 6A:
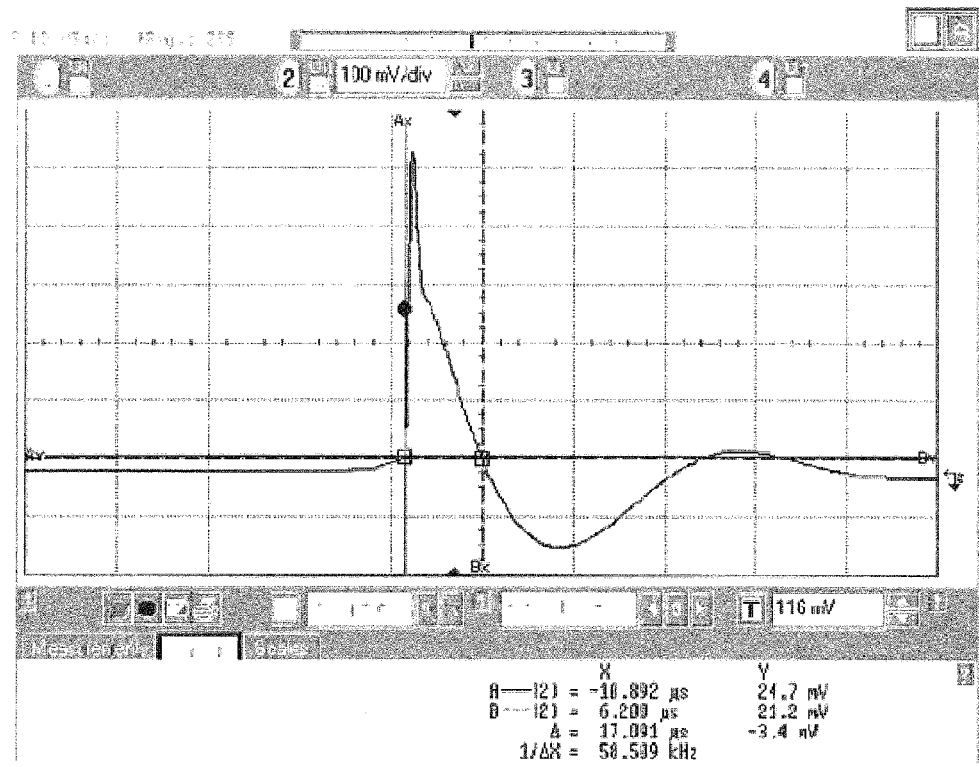
FIGS. 6a and 6b shows, respectively the square wave response of an SOI-CMOS hot film sensor at a resistance overheat ratio of 0.4, showing a measured time constant of 13.8 μs, corresponding to a cut-off frequency of 48 KHz; and a graph of sensor frequency response against sensor resistive overheat ratio, illustrating that the frequency response improves significantly with increased overheat ratio.
Figure 6B:
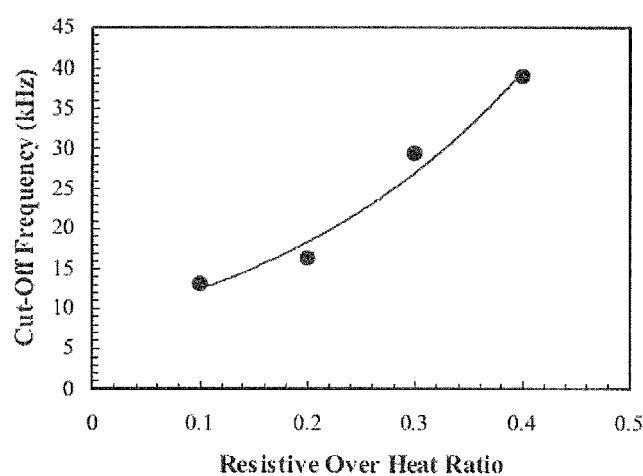
Figure 7A:
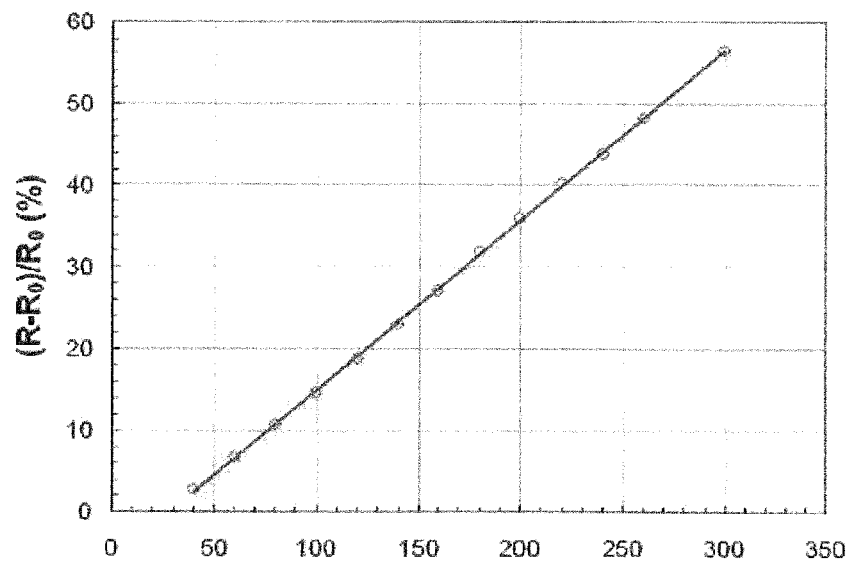
Figure 7B:
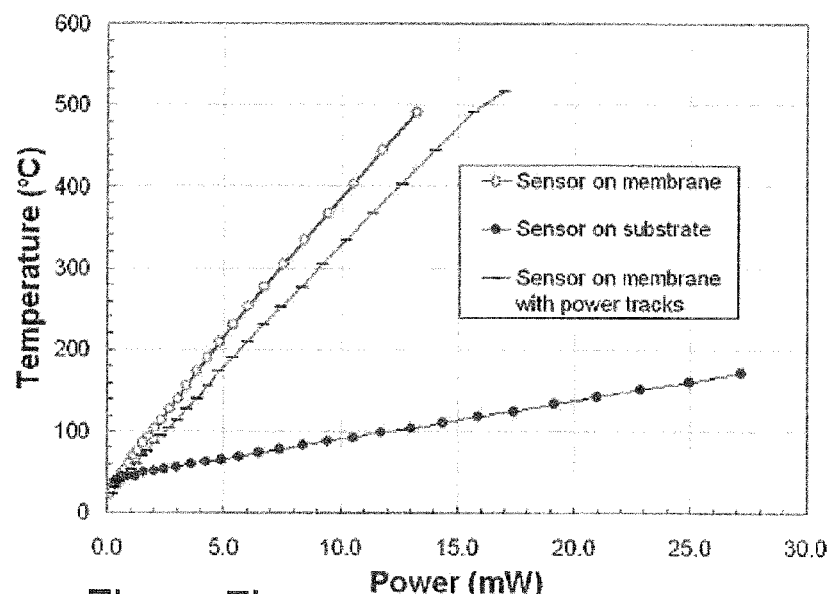

The frequency response and time constants of a hot-wire (or hot film) sensor can be estimated by injecting a sine wave or square wave signal into a CT circuit (P. Freymuth, "Frequency-response and electronic testing for constant-temperature hotwire anemometers," J. Phys. E: Sci. Instr., vol. 10, pp. 705-710, 1977). We used a square wave injection method to determine the time constant $t_c$ and the frequency response $f_c$ of our sensor. The sensor exhibits a time constant of 13.8 µs (FIG. 6). According to the relation $f_c=1/(1.5\ t_c)$, the corresponding cut-off frequency is estimated to be 48 KHz. This frequency response and time constant is an improvement on prior art hot film shear stress sensors.

A sensor may be fabricated in a range of sizes: the frequency response of a 130 µm×130 µm aluminium sensor was 39 KHz; that of a 18.5 µm squaresensor was up to 122 KHz.

Tungsten

Some preferred embodiments of the sensor use (CMOS) tungsten as the sensing element. This provides low thermal conductivity (reduced heat loss through the power tracks), increased electrical resistivity (increased Joule heating), and greater robustness (high strength, and high temperature operation). Embodiments of the CMOS sensor are fabricated using all-tungsten process (no aluminium is used in the chip). This is also true of the circuits shown later, for example the circuit of FIG. 8 (and other similar examples which follow)— preferably the electronic driver/interface circuits also employ an all (only) tungsten process—with no aluminium. Although the increased resistance of using tungsten circuits may, for example, reduce output signal level this is compensated by the improved sensor performance. In embodiments sensor operation at temperatures greater than 300° C., 400° C. or 500° C. is possible with a frequency response of >300 KHz, 400 HKz or 500 KHz, for example approaching 1 MHz.

Figure 8:
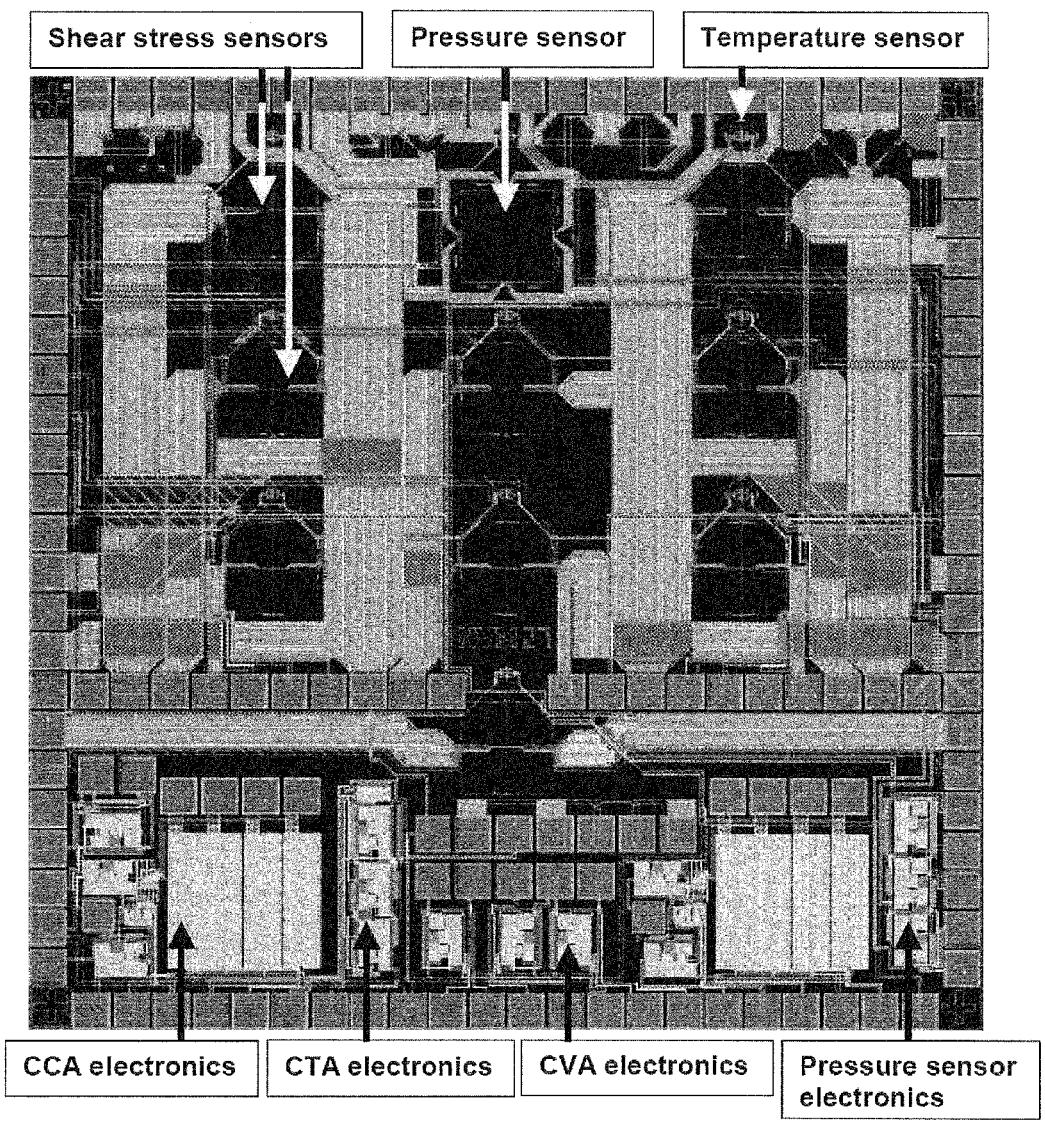
FIG. 8 shows an example of an array of nine shear stress sensors, along with their interface electronic circuits, both fabricated during the same CMOS fabrication process on the same chip/die of size 3.8 mm square. These shear stress sensors have been made from CMOS metal layer (i.e. aluminium and tungsten). The interface electronics includes anemometry circuits for driving sensors in either of the three, i.e. constant temperature (CT), constant voltage (CV) or constant current (CC), modes. The chip also has a pressure sensor and nine temperature sensors for multiple flow parameters measurement simultaneously.

Examples of CMOS Wall Shear Stress Sensors' Layout With and Without Electronics Integration An example of shear stress sensors integrated with their interface electronic circuits on the same CMOS SOI chip of size 3.8 mm square, both fabricated during the same CMOS fabrication process is shown in FIG. 8. As annotated and shown on the figure, there are nine shear stress sensors made from CMOS metals (i.e. aluminium and tungsten) on the chip. To drive these sensors in a constant temperature (CT), constant voltage (CV) or constant current (CC) mode, all three types of drive anemometry circuits (i.e. CTA, CVA and CCA) have also been fabricated during the same CMOS fabrication steps. To measure other critical parameters of the fluid under investigation, a pressure sensor with its electronics and nine temperature sensors have also been fabricated on the same chip/die. If needed, a suitable drive and control circuit for the temperature sensors could also be integrated on the same chip/die. For this particular chip, the sensor connection pads are kept on the top surface. However, these pads can be easily replaced by flip chip bumps on the lower side of the silicon/SOI substrate by using, for example, Silex high density through wafer vias technology (e.g. Tomas Bauer, "High Density Through Wafer Via Technology," NSTI-Nanotech 2007, www.nsti.org, ISBN 1420061844 Vol. 3, 2007, pp 116-119) to avoid bonding wires' interference with fluid flow. We fabricated a device of the type shown in FIG. 8 and found it to provide 65 mV sensor output voltage, using a CCA circuit, at 0.5 Pa.

Figure 9:
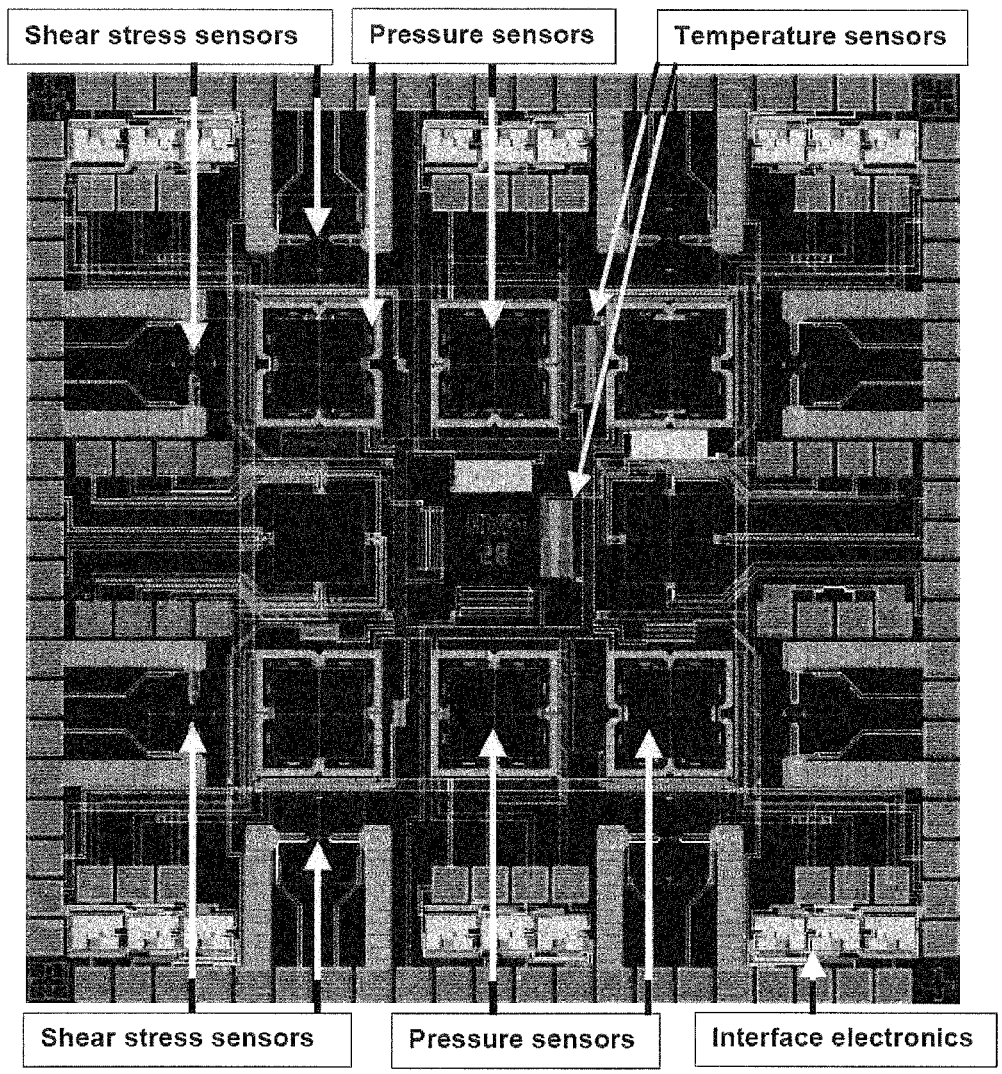
FIG. 9 is an example of 8 shear stress sensors, 12 temperature sensors and 8 pressure sensors along with their interface electronics fabricated during the same CMOS fabrication process on the same chip/die of size 3.8 mm square. The shear stress sensors are hot-film strip type with a length and width of 80 μm and 2.5 μm respectively and have been made from CMOS metal layer (i.e. aluminium and tungsten). Their membranes are of different shapes (i.e. circular and square) with diameters/side lengths of 80, 160, 240 and 320 µm. The pressure sensors use different sensing materials and are piezo resistive, piezo junction and piezo MOS types.

Another example of integrated CMOS shear stress sensors is shown in FIG. 9. In this chip/die, there are eight shear stress sensors, eight pressure sensors and 12 temperature sensors. In this design, the hot film shear stress sensors and their resistance sensing lines have been made from the intermediate or middle metal layer, whereas the tracks for power (or current) supply have been made using all three metal layers interconnected with metal vias to keep the track resistance and hence associated power loss to a minimum. The shear stress sensing hot film has a simple rectangular shape (size 80×2 µm) whereas the silicon oxide membrane formed by DRIE has either a circular or square shape. The diameters of circular shaped membranes are 80, 160, 240 and 320 µm. Similarly, the side length of square shaped membranes are also 80, 160, 240 and 320 µm. The variation in membrane sizes and shapes allows for investigation of their effects on sensors' power consumption, frequency response and sensitivity; and membranes' mechanical robustness. For further comparison, the membranes of triangular, elliptical, pentagon, hexagonal, heptagon, and octagonal shapes may also be fabricated during DRIB process. The pressure sensors on this chip use different materials (e.g. poly silicon, p-silicon, n-silicon, p well silicon, n well silicon etc) to exploit variation in their piezo-resistivity for having different pressure sensitivities and measurement ranges within one chip/die. Other pressure sensors use CMOS fabricated p-n diodes and MOSFETs to explore piezo junction effect and piezo-MOS effect based pressure sensors. The temperature sensors shown in this figure are all thermistor type, with different sizes (covering for example from 30 µm×50 µm to 400 µm×100 area), different materials (e.g. CMOS metal, poly silicon, n-silicon, p-silicon etc) and different resistances (and hence different temperature sensitivities). Other CMOS temperature sensors (e.g. diode type) can also be fabricated/integrated on the same chip.

Figure 10:
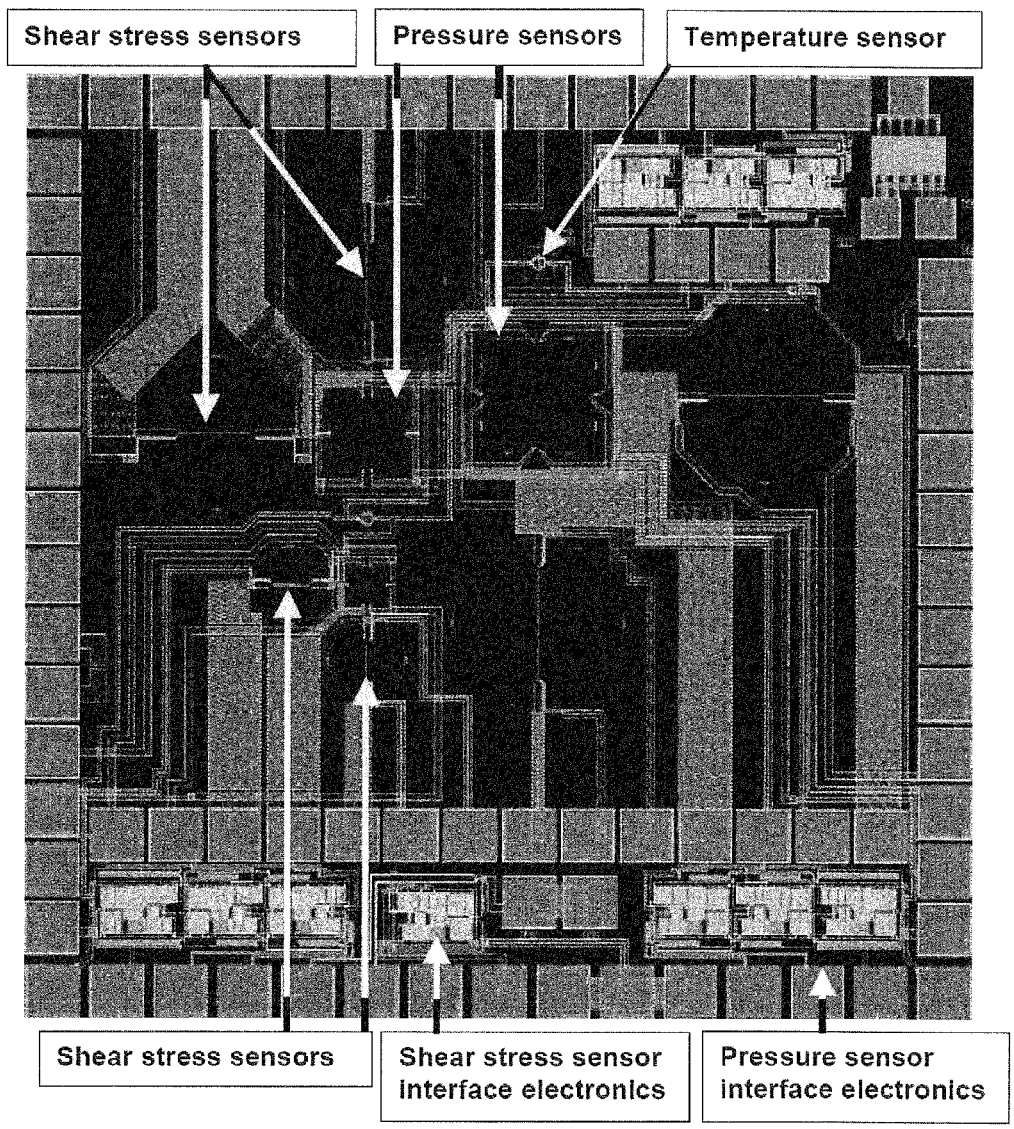
FIG. 10 shows an example of a CMOS integrated sensor chip having three pairs of hot film shear stress sensors of rectangular strip shape (sizes 300 µm×4 µm, 200 µm×3 µm and 100 µm×3 µm) on silicon oxide membranes (of diameter size 450 µm, 300 µm and 200 µm respectively). The shear stress sensors can resolve the horizontal and vertical component of flow shear stress at the same time. For correlation with pressure and temperature variations, piezo-resistive type pressure sensors (square shape with side lengths of 300 µm, 200 µm and 100 µm, respectively) and diode type temperature sensors have also been fabricated next to the shear stress sensors. The chip/die also has constant voltage anemometry and pressure sensor electronics integrated on the same chip.

A third example of a CMOS integrated sensor chip having shear stress sensors and is associated electronics on the same chip is shown in FIG. 10. In this case three shear stress sensors having rectangular strip shape hot films (sizes 3 µm×300 µm, 2 µm×200 µm and 1.5 µm×100 µm) on silicon oxide membranes (of diameter size 450 µm, 300 µm and 200 µm respectively) have been fabricated which can resolve the horizontal and vertical component of flow shear stress at the same time. For correlation with pressure variations, piezoresistive type pressure sensors (square shape with side lengths 300 µm, 200 µm and 100 µm) have also been fabricated next to the shear stress sensors. To pick up the flow temperature, diode type temperature sensors have also been fabricated in front of each set of shear stress and pressure sensor. Hence this provides a fully CMOS, drive circuit integrated multi sensor chip to measure some or all of shear stress (preferably both horizontal and vertical components), pressure and temperature of a fluid at the same time. To drive these shear stress and pressure sensors, electronic circuits for CVA (constant voltage anemometry) and pressure sensors signal amplification have been integrated on the same chip. Embodiments of the sensors we describe provide enhanced thermal isolation in addition to providing other novel and advantageous features.

In embodiments we integrate a CVA (constant voltage anemometry) circuit with a micro machined shear stress sensor. This integration is preferably with sensors that use the metals available in the same CMOS fabrication process in which the CVA circuit is fabricated.

Combining the sensor and electronics on a single chip has the advantage of low manufacturing cost and ease of packaging. However in other applications, particularly high temperature applications (e.g. turbo-machinery, aircraft or automobile engines etc) the sensor may be fabricated as described above using a CMOS process but the electronics may be mounted separately, remote from the sensor. This enables the sensor to operate at higher temperatures than those, which the electronics can readily withstand.

For such high temperature applications, instead of aluminium, sensors made from CMOS tungsten metallization is preferably used. Also, for applications involving high temperatures, high vibrations levels (e.g. aero-engines, turbomachinery, car engines etc) and/or which need very high mechanical strength of the membranes (i.e. for deep water applications e.g. on sub-marines), the cavity etched under the membranes may be filled with a flexible polymer material which has suitable physical and thermal properties for that particular application (e.g. a low thermal conductivity, high temperature resistance, low coefficient of thermal expansion, low water absorption coefficient, bio compatibility and the like).

Figure 11:
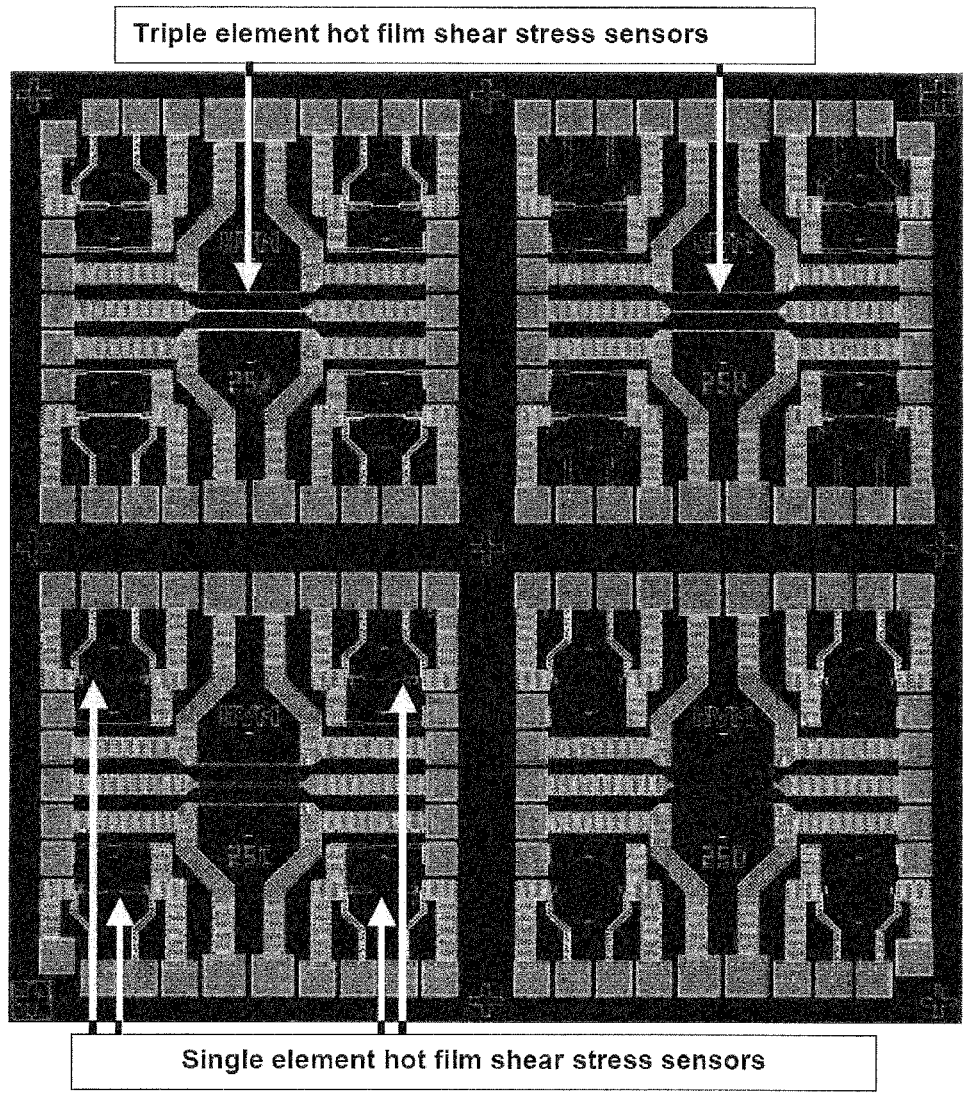
FIG. 11 shows an example of sensor chip/die which, for example, does not has its interface electronics on the same chip.

To exemplify such a case, where no circuits are fabricated on the sensor chip and are rather fabricated on separate chips, we also show some single and multiple hot film shear stress sensors without any on-chip electronics in FIG. 11. For a range of applications and variable performance parameters, these rectangular strip shaped hot-film sensors have been made with different CMOS metal layers and different widths and lengths (e.g. widths vary from 1, 1.5, 2, 2.5, 3, 5, 10, 15, 20 μm and length varies from 50, 100, 150, 200, 400 μm). For example for same width, a shear stress sensor with a longer hot film will have more sensitivity, but reduced resolution, lower cut-off frequency response and higher power consumption, and vice versa. To compare the effect of silicon oxide membranes on thermal isolation of the sensor, the sensors with same dimensions have also been fabricated on SOI substrate.

Examples of Sensor Embodiments

Figure 12:
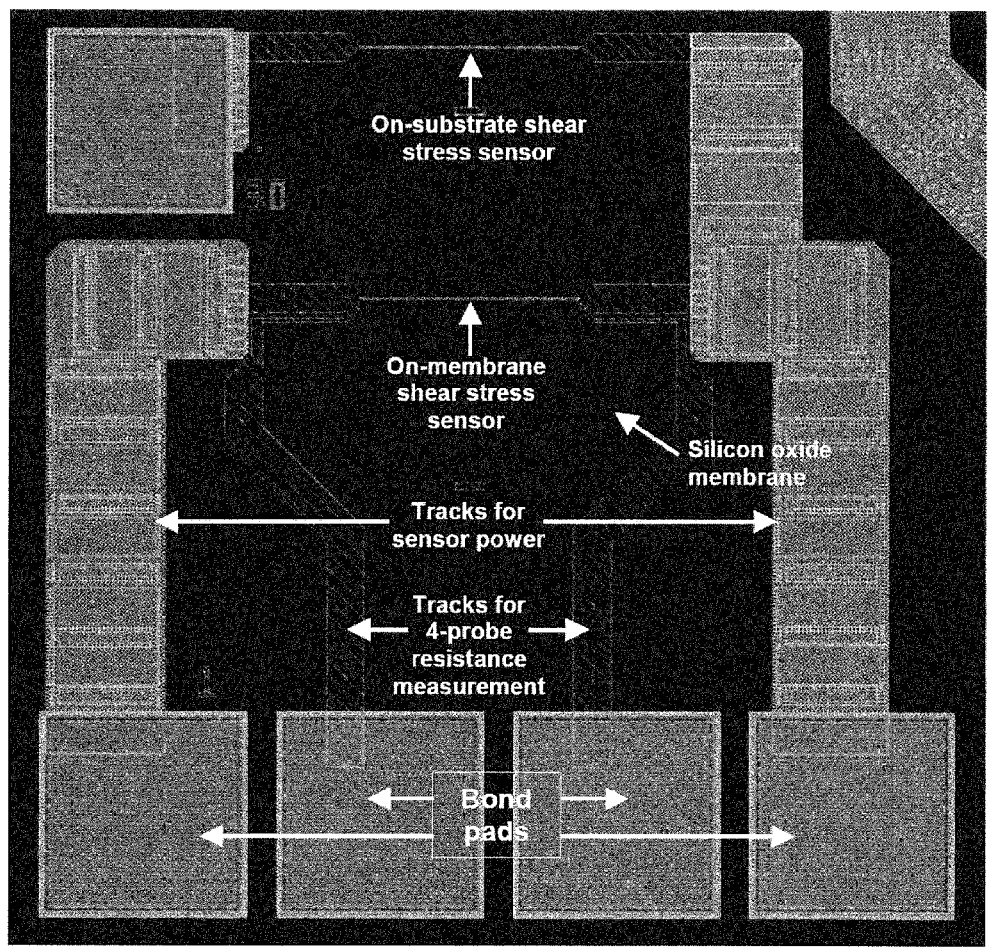
FIG. 12 show two rectangular strip shaped hot film shear stress sensors (with and without silicon oxide membrane underneath. For precise resistance measurements of the sensor, separate tracks for current and voltage monitoring using a 4-probe method have been provided.

We have described the performance of only one, aluminium based, meander shaped CMOS shear stress sensor in this description. However, there is a range of alternate sensor embodiments with hot films of different shapes that have been designed and fabricated (or could be designed and fabricated) within the same (or similar) CMOS process (or processes). For example, instead of a meander shape, the resistive aluminium or tungsten track used as a shear stress sensor could be of a circular, elliptical, triangular or any other suitable shape. Yet in other embodiments, we may simply use a long rectangular strip (which has length>>width) as a shear stress sensing element (see FIG. 12).

In the CMOS process employed for fabrication of these sensors, for example three metal layers may be employed (see FIG. 1a). The resistive hot film sensor may be laid in any one of these three metal layers, with the upper most layer expected to give maximum sensitivity as a shear stress sensor due to heat being lost to the fluid the quickest. In yet other CMOS processes, even four or five metal layers could be available and hence any one or more than one of these layers could be utilized for fabrication of multiple hot film sensing structures.

For example, two layers of metal (one on top of the other with a silicon oxide layer between them) could be used to achieve redundancy; if one burns due to excessive electric power or for any other reason, the second hot film at the same horizontal but at different vertical location within the metal/silicon oxide sandwich structure could be used. Or two or three hot-films could be embedded at the same location and operated simultaneously to achieve a higher temperature at one spot.

In one such embodiment, we have laid a hot film in middle metal layer to grow on-chip CNTs on the upper surface of the silicon oxide membranes (e.g. as reported by M. Samiul Hague, Syed Zeeshan Ali, Nalin Rupensinghe, Ibraheem Haneef, Prasanta Guha, Florin Udrea, William I. Milne, Jonghyurk Park, Sunglyul Maeng, "Novel On-Chip Growth of Carbon Nanotubes using High Temperature Microheaters,", Proc. $8^{th}$ Intnl. Conference on Science and Application of Carbon Nano Tubes-CNT07, Brazil, 24-29 Jun. 2007, pp 15, for growing vertically aligned CNTs). Alternatively a technique for growing vertically aligned CNTs such as that described in WO2006/087588 may be employed.

For direct on-chip CNT growth, first a thin layer (e.g. 2~3 nm) of catalyst (e.g. iron or nickel) is deposited onto the sensor chip using a magnetron sputter deposition system or thermal evaporator. After deposition of the catalyst layer, the chip is transferred to the CNT growth chamber, with provision of electrical connections to the tungsten heater of the CMOS chip which acts as a thermal source during the local growth of the carbon nanotubes. The chamber is then pumped down to a base pressure of $2 \times 10^{-1}$ mbar or lower using a rotary pump. At this stage the micro heater is powered by external power source and heated to an optimized temperature (e.g. 650° C. or higher) for the growth of CNTs. After few minutes, the catalyst layer converts into small islands and at this stage Ammonia ($NH_3$) and Acetylene ($C_2H_2$) in the ratio of 4:1 (200:50)sccm is released onto the chamber for the deposition of CNTs. This process is continued for few minutes during which the CNTs grow locally on the silicon/ nitride/oxide membrane. This method grows entangled CNTs but these nonetheless provide a good heat sink.

Figure 13:
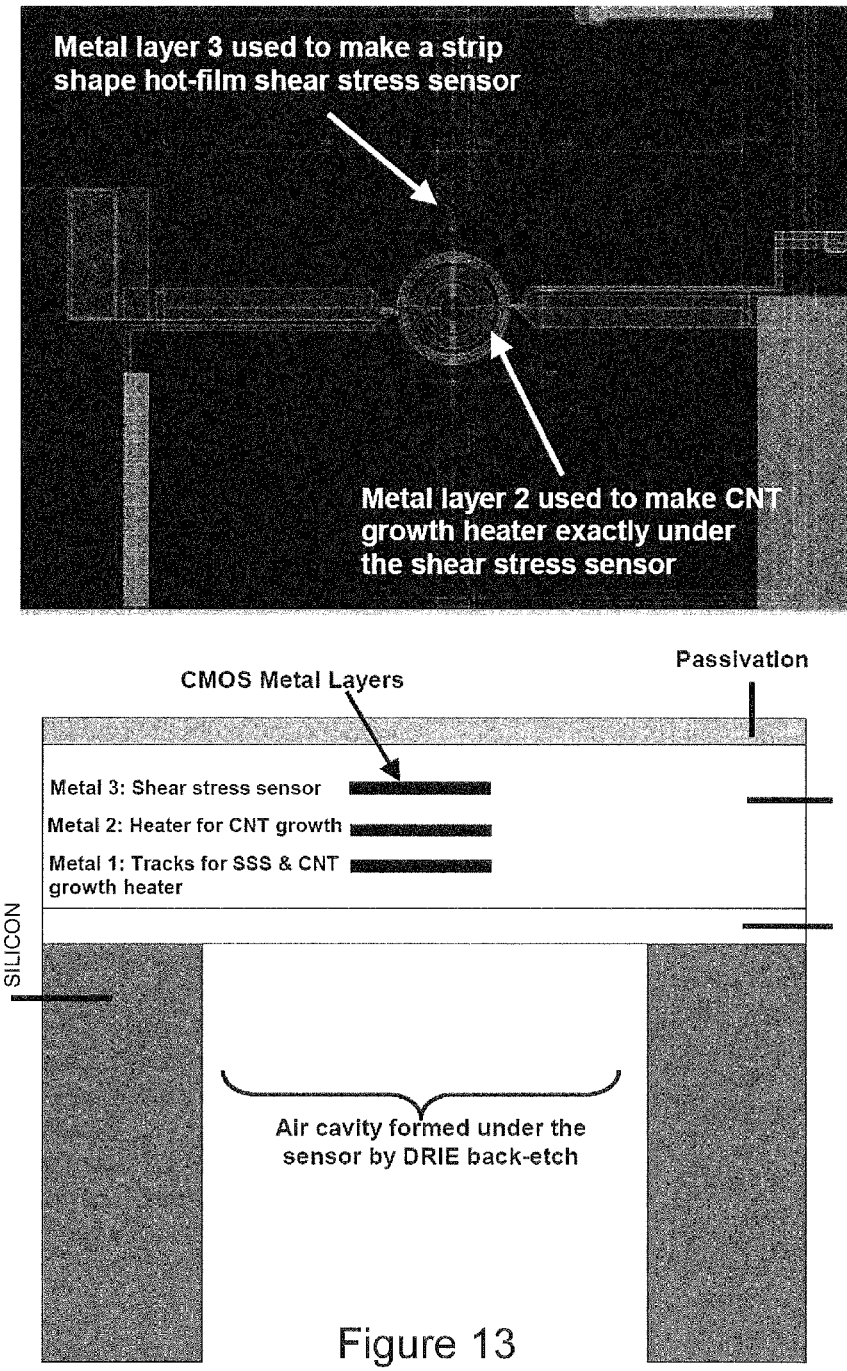
FIG. 13 elaborates one of the sensor embodiment showing a shear stress sensor made from the top metal layer (metal 3). To enhance its sensitivity, CNTs may be grown in the middle part of shear stress sensor by using another heater, which is made of the middle metal layer (metal 2). Both shear stress sensor and CNT growth heater have separate power supply tracks.

After CNTs growth, the rectangular strip type hot film sensor fabricated in the top layer can be used as a shear stress sensor. Since CNTs have a very high thermal conductivity (i.e. more than 3000 W/m-K, as reported by P. Kim, L. Shi, A. Majumdar and P. L. Mceuen (2002) Mesoscopic thermal transport and energy dissipation in carbon nanotubes. *Physica B: Condensed Matter,* 323, 67-70) the heat generated by the sensor will be mostly escaped through the CNTs into the air and hence increase the sensor sensitivity. An example of such an embodiment is shown in FIG. 13.

In other embodiments, the top layer of metal could be used to make a heat spreading, plate shaped structure above the hot film (or films) laid down on the middle or the lowest (or both lower and middle) metal layer (or layers). This arrangement will also increase the sensor sensitivity.

Figure 14A:
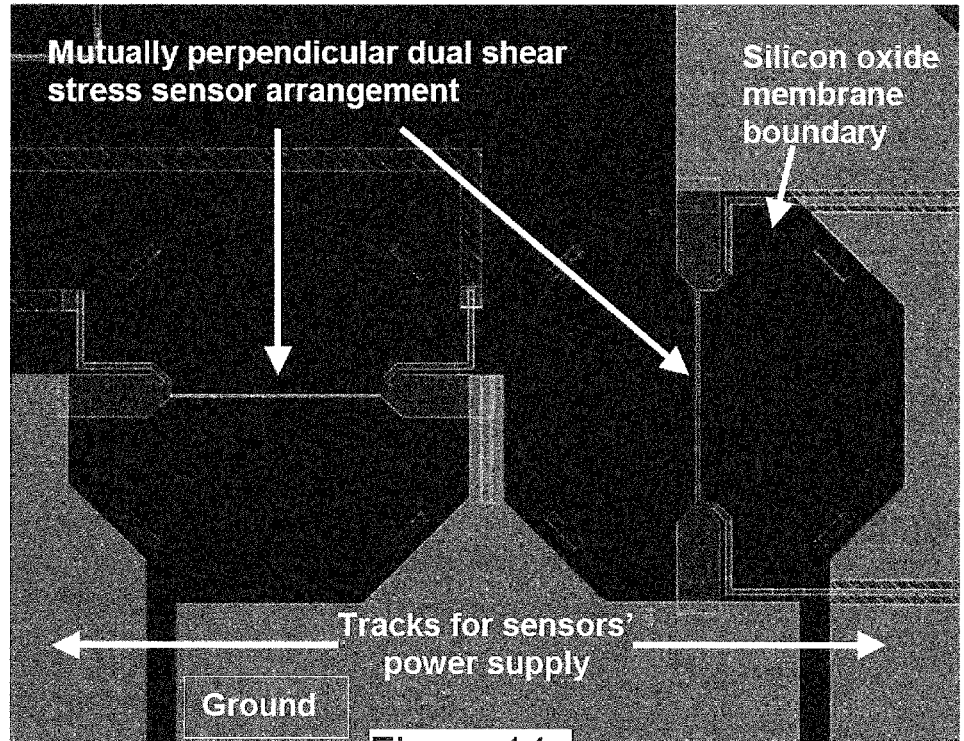
FIG. 14(a) shows a sensor embodiment showing a shear stress sensor made from the top metal layer (metal 3). To enhance its sensitivity, CNTs may be grown in the middle part of shear stress sensor by using another heater, which is made of the middle metal layer (metal 2). Both shear stress sensor and CNT growth heater have separate power supply tracks.
Figure 14B:
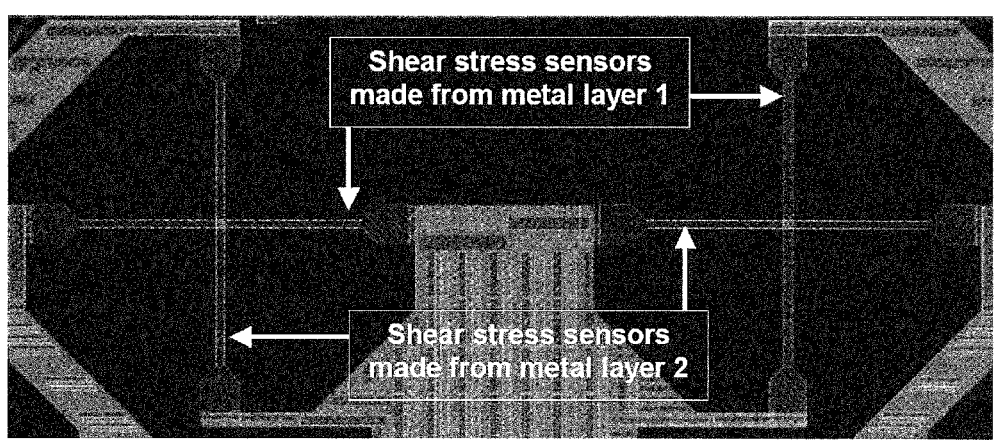
FIG. 14(b) explains another sensor embodiment showing two pairs of mutually perpendicular shear stress sensors which have been made from different metal layer. If one pair of sensors gets damaged during operation, the other pair may be readily used.
Figure 15:
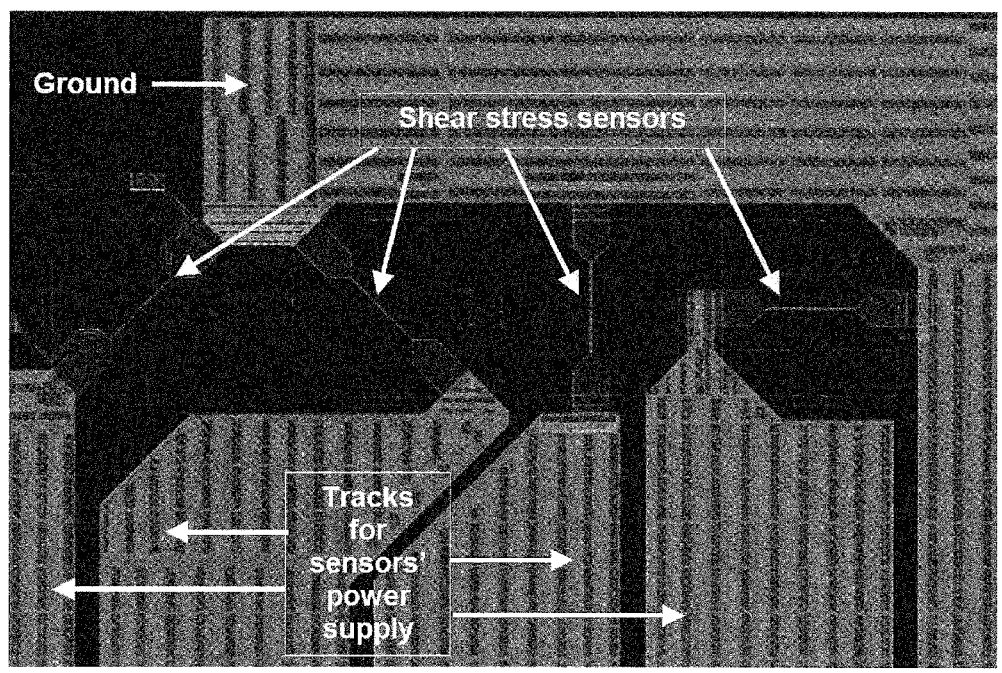
FIG. 15 is a sensor embodiment showing four shear stress sensors, for ultra fine resolution shear stress measurements. The sensors have a length and width of 50 µm and 1.25 µm respectively and can resolve flow shear stress components at 0, 45, 90 and 135° angles simultaneously.

In another embodiment, two hot films may be embedded in different layers but perpendicular to each other and used for measuring the vertical and horizontal component of wall shear stress simultaneously. An example of such an embodiment having one and two pairs of mutually perpendicular sensors is shown in FIGS. 14a and 14b. For ultra high resolution of wall shear stress components at different angles (e.g. 0, 45, 90, 135 degree etc), fours hot film sensors with a length of 50 μm have been fabricated and shown in FIG. 15.

Figure 16:
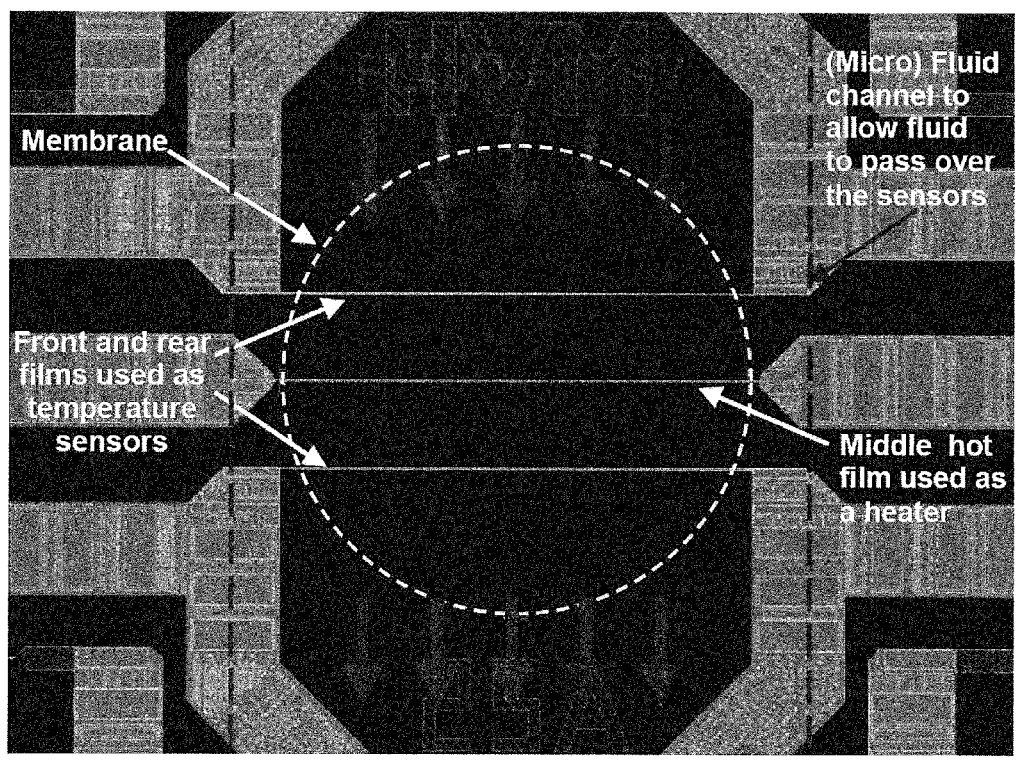
FIG. 16 shows a triple hot film sensor arrangement that can also be used as a Time of Flight (TOF) or calorimetric flow sensor for measuring the flow rate, flow speed or flow direction of fluids. The middle hot film sensor would act as a heater and the ones on both sides (front and rear) will act as temperature sensors for these applications.

In one embodiment, three parallel hot film strips based sensor arrangement can be used as a time of flight (TOF) flow sensor (see FIG. 16). A TOF flow sensor of this design comprises an upstream heater and a downstream thermal sensor. During the measurement, a short heat impulse is injected into the fluid by the upstream heater and detected by the downstream thermal sensor. The time difference between two signals is related to the volumetric flow rate of the fluid or the fluid velocity (M. Ashauer, H. Glosch, F. Hedrich, N. Hey, H. Sandmaier, W. Lang, "Thermal flow sensor for liquids and gases based on combinations of two principles," Sensors and Actuators A: Physical. 1999; 73(1-2):7-13; R. J. Rodrigues, R. Furlan, "Design of microsensor for gases and liquids flow measurements," Microelectronics Journal. 2003; 34(5-8): 709-11; J. Van Kuijk, T. S. J. Lammerink, H. E. De Bree, M. Elwenspoek, J. H. J. Fluitman, "Multi-parameter detection in fluid flows," Sensors and Actuators A: Physical. 1995; 47(1-3):369-72; C. Yang, M. Kummel, H. Soeberg, "Dynamic model for a thermal transit-time flow sensor," Chemical Engineering Science, 1991; 46(3):735-40; C. Yang, H. Soeberg, "Monolithic flow sensor for measuring millilitre per minute liquid flow," Sensors and Actuators A: Physical. 1992; 33(3): 143-53).

Similarly, the same three strip hot film embodiment shown in FIG. 16 can also be used as a calorimetric flow sensor to detect flow velocity, flow rate or the flow direction based upon the three-element calorimetric measurement principle by which the heat transferred from a heated solid element to a fluid is transported by forced convection, causing the temperature of two sensing elements placed at both sides to change. The flow response is obtained from the difference of the temperature between the two sensing elements. At zero flow, the symmetrical temperature distribution is achieved by heat conduction through the supporting material of the heater (membrane) as well as through the surrounding air. However, under the presence of an incoming flow, the effects of forced convection make this temperature distribution to change, that is, as the heat dissipated by the heater is transported by the flow, there is a cooling effect in the upstream zone whereas there is an increase in temperature downstream (N. Sabate, J. Santander, L. Fonseca, I. Gracia, C. Cane, "Multi-range silicon micromachined flow sensor," Sensors and Actuators A: Physical. 2004; 110(1-3):282-8). Apart from aluminium and tungsten, these triple element flow sensors have been fabricated using p-doped silicon and polysilicon as well for comparing their performance with metal based CMOS hot film sensors. Further, this particular embodiment may be used for flow separation or flow reversal detection on aerodynamic surfaces (cf. U. Buder, R. Petz, M. Kittel, W. Nitsche, E. Obermeier, "AeroMEMS polyimide based wall double hot-wire sensors for flow separation detection,", Sens. Actuators A: Phys. (2007), doi:10.10161j.sna.2007.04.058, in press) and in medical applications (Al-Salaymeh A, Jovanovic J, Durst F. Bi-directional flow sensor with a wide dynamic range for medical applications. Medical Engineering & Physics. 2004; 26(8):623-37.

Figure 17:
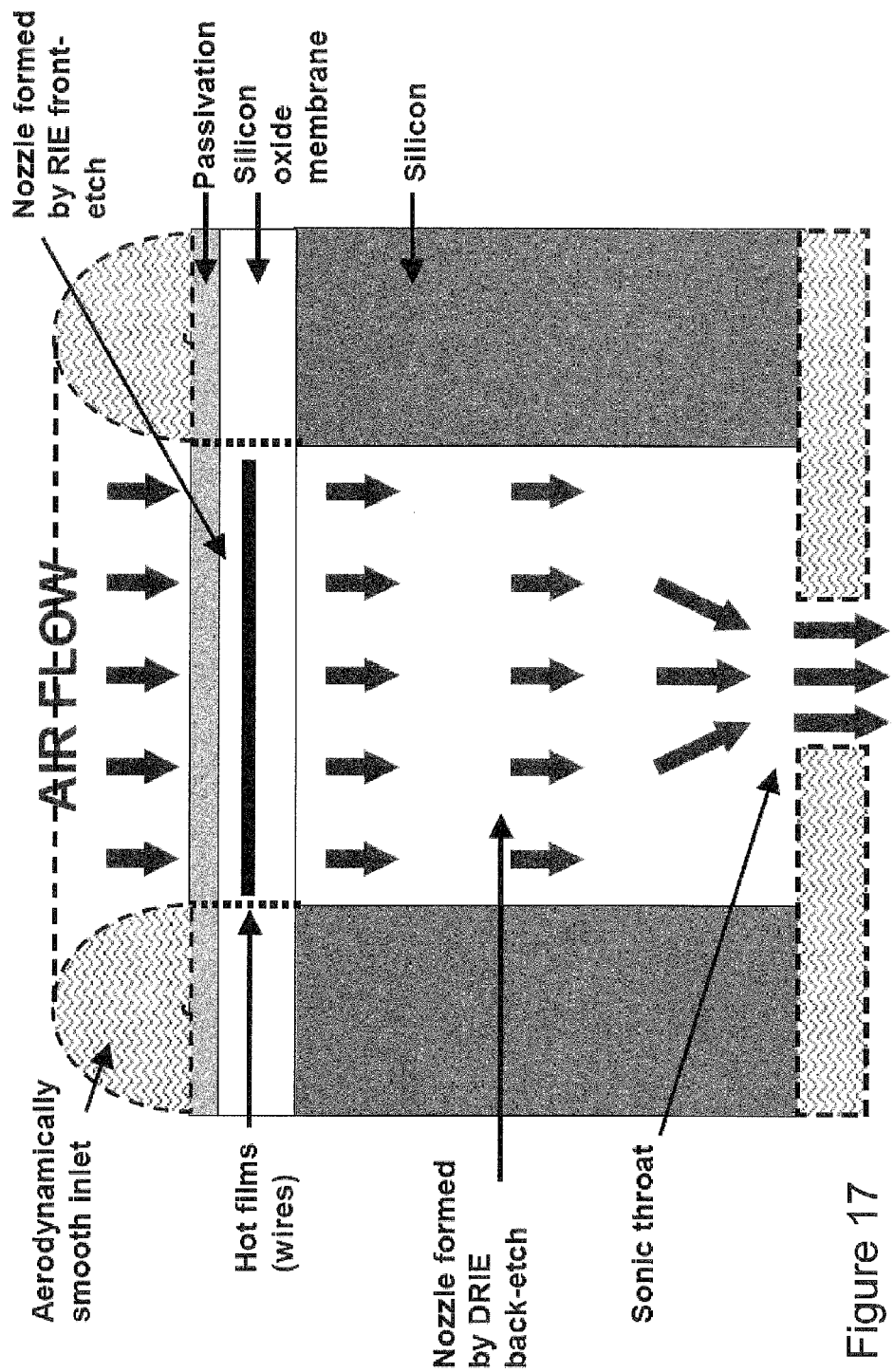
FIG. 17 shows the top view (upper) and vertical cross-sectional view (lower) of the dual hot wire MEMS aspirating probe that is fabricated using the CMOS metal hot films. By doing an extra front etch and by adding a suitable inlet and outlet to the chip, a triple hot film shear stress sensor (e.g. shown in FIG. 16) can be used as a CMOS MEMS dual hot-wire aspirating probe.

The same embodiment of triple hot film strips type shear stress sensor (FIG. 17) may also be used as a high frequency dual hot wire temperature and pressure aspirating probe for unsteady compressible flows W. F. Ng, A. H. Epstein, "High-frequency temperature and pressure probe for unsteady compressible flows," Review of Scientific Instruments. 1983; 54:1678 S. J. Payne, R. W. Ainsworth, R. J. Miller, R. W. Moss, N. W. Harvey, "Unsteady loss in a high pressure turbine stage," International Journal of Heat and Fluid Flow. 2003; 24(5):698-708; C. H. Sieverding, T. Arts, R. Denos, J. F. Brouckaert, "Measurement techniques for unsteady flows in turbomachines," Experiments in Fluids, 2000; 28(4):285-321)). The middle wire and the mebrane of the sensor may be etched using for example a fron reactive ion etch (RIE) step to make free standing dual hot wires (see upper picture in FIG. 17). Then by adding suitable inlet and an exit blocks (see lower schematic diagram of FIG. 17) this dual hot wire probe will allow the air flow to pass through it. By operating both the hot films (or wires) at different temperature in separate constant temperature anemometer circuits, two simultaneous voltage measurements may be made from which the total pressure and total temperature of the fluid passing through the probe can be determined. The detailed equations used in this technique may be seen in W. F. Ng, A. H. Epstein, "High-frequency temperature and pressure probe for unsteady compressible flows," Review of Scientific Instruments. 1983; 54:1678 and are not given here.

We have described a hot film shear stress sensor fabricated on a silicon substrate with a thin silicon oxide insulating layer in which a hot film comprising a CMOS compatible metal is embedded. The metal may be a high temperature metal (tungsten) or a low temperature metal (aluminium). Surprisingly we have found that CMOS-based aluminium metallization is viable as a hot film shear stress sensing element. As one of the final fabrication steps the substrate is back-etched by a single DRIE step so as to form a thin membrane in the sensing area for thermal isolation of the hot film. This back etch is performed post-CMOS but in embodiment all the other layers including the resistive hot film are fabricated using a CMOS process employing aluminium or tungsten metallization. Thus the device can be monolithically integrated with drive, control and transducing circuitry using low cost CMOS processing. Since the hot film, insulating layer, and the other layers are fabricated within the CMOS sequence they do not require extra masks or processing. Further, the sensors perform well, having a high TCR, very lower power consumption and a high frequency response, as well as having very good reproducibility from sensor to sensor and from wafer to wafer.

No doubt many other effective alternatives will occur to the skilled person. It will be understood that the invention is not limited to the described embodiments and encompasses modifications apparent to those skilled in the art lying within the spirit and scope of the claims appended hereto.

What is claimed is:

1. A hot film shear stress sensor comprising a silicon substrate supporting a membrane having a cavity underneath, said membrane bearing a film of metal and having electrical contacts for heating said film, and wherein said membrane comprises a silicon oxide membrane, wherein said metal comprises aluminium or tungsten, and wherein said membrane has a protective layer of a silicon-based material over said film of metal and wherein said sensor is fabricated by a CMOS process, wherein said silicon substrate is of a silicon on insulator (SOI) type, wherein said film of metal comprises a plurality of stacked metal layers.

2. A hot film shear stress sensor as claimed in claim 1, wherein said cavity is formed by deep reactive ion etching (DRIE).

3. A hot film shear stress sensor as claimed in claim 1 wherein the sensor has a temperature coefficient of resistance (TCR) of greater than 0.2%.

4. A hot film shear stress sensor as claimed in claim 1 wherein said film of metal defines a meander pattern.

5. A hot film shear stress sensor as claimed in claim 1 having four said electrical contacts for four-wire sensing.

6. A hot film shear stress sensor as claimed in claim 1 wherein said protective layer comprises a layer of oxide or nitride.

7. A hot film shear stress sensor as claimed in claim 1 wherein said electrical contacts comprise the same metal as said film, and wherein said film of metal and said electrical contacts comprise a single layer of said sensor.

8. A hot film shear stress sensor as claimed in claim 1 wherein one or both of said membrane and said protective layer comprises a plurality of stacked silicon oxide layers.

9. A hot film shear stress sensor as claimed in claim 1 wherein said film of metal comprises at least two metal layers, said two metal layers including an upper metal layer closest said protective layer and a lower metal layer under said upper metal layer, and wherein said upper metal layer has one or both of a larger surface area and a different lateral shape to said lower metal layer.

10. A hot film shear stress sensor as claimed in claim 1 further comprising a heat sink in thermal contact with said film of metal.

11. A hot film shear stress sensor as claimed in claim 10 wherein said heat sink comprises vertically-aligned carbon nanotubes.

12. A hot film shear stress sensor as claimed in claim 1 wherein said metal comprises aluminium.

13. A hot film shear stress sensor as claimed in claim 1 wherein said metal comprises tungsten.

14. A hot film shear stress sensor as claimed in claim 1 further comprising a temperature sensor within the membrane, in thermal contact with said film.

15. A CMOS sensor integrated circuit comprising a sensor as claimed in claim 1 integrated on a common substrate with an electronic interface comprising one or more of drive, control and read-out circuitry for said sensor.

16. A method of fluid flow sensing using a hot film shear stress sensor as claimed in claim 1, the method comprising:
  providing a hot film shear stress sensor comprising a silicon substrate supporting a membrane having a cavity underneath, said membrane bearing a film of metal and having electrical contacts for heating said film, wherein said membrane comprises a silicon oxide membrane, wherein said metal comprises aluminium or tungsten, wherein said membrane has a protective layer of a silicon-based material over said film of metal; and wherein said sensor is fabricated by a CMOS process;
  applying electrical power to said electrical contacts to heat said film of aluminium and tungsten metal;
  flowing a fluid past said heated film of metal;
  measuring an electrical response of said heated film of metal to said flowing fluid, wherein said electrical response is a response which measures a degree of heat transfer from said heated film of metal to said flowing fluid; and
  determining a fluid flow parameter relating to a rate of flow of said fluid from said measured electrical response which measures a degree of heat transfer from said heated film of metal to said flowing fluid.

17. A method as claimed in claim 16 wherein said fluid flow parameter comprises a shear rate or shear stress in said flowing fluid.

18. A method as claimed in claim 16 wherein said fluid flow sensing comprises resolving one or more orthogonal components of said fluid flow parameter relating to said rate of flow of fluid.

19. A hot film shear stress sensor comprising a silicon substrate supporting a membrane having a cavity underneath, said membrane bearing a film of metal and having electrical contacts for heating said film, said hot film shear stress sensor further comprising a heat sink in thermal contact with said film of metal, wherein said silicon substrate is of a silicon on insulator (SOI) type, wherein said heat sink comprises vertically-aligned carbon nanotubes.

20. A method of fabricating a hot film shear stress sensor on a silicon substrate, the method comprising:
  fabricating a layer of silicon oxide in a sensing region of said substrate, said silicon substrate is of a silicon on insulator (SOI) type;
  fabricating a film of metal on said layer of silicon oxide on said sensing region, said metal comprising aluminium or tungsten, wherein said film of metal comprises a plurality of stack metal layers;
  fabricating electrical contacts for said film;
  using deep reactive ion etching to undercut said layer of silicon oxide to leave a cavity underneath; and
  fabricating a protective layer over said film of metal.

21. A method as claimed in claim 20 wherein said electrical contacts are fabricated from the same metal as said film and wherein said fabricating of said film and said fabricating of said electrical contacts are performed in a single, common step.

* * * * *